United States Patent
Lee et al.

(10) Patent No.: US 12,005,269 B1
(45) Date of Patent: Jun. 11, 2024

(54) HANDPIECE FOR SKIN LASER TREATMENT AND MEDICAL LASER TREATMENT APPARATUS INCLUDING THE SAME

(71) Applicant: Bisonmedical Co., Ltd., Seoul (KR)

(72) Inventors: Sunwoo Lee, Seoul (KR); Woohyek Choi, Yongin-si (KR); Jeonghee Kim, Siheung-si (KR)

(73) Assignee: Bisonmedical Co., Ltd., Seoul (KR)

( * ) Notice: Subject to any disclaimer, the term of this patent is extended or adjusted under 35 U.S.C. 154(b) by 0 days.

(21) Appl. No.: 18/489,031

(22) Filed: Oct. 18, 2023

(30) Foreign Application Priority Data

Jan. 17, 2023 (KR) .................. 10-2023-0006892

(51) Int. Cl.
  *A61N 5/067* (2006.01)
  *A61N 5/00* (2006.01)
  *A61N 5/06* (2006.01)

(52) U.S. Cl.
  CPC ........ *A61N 5/067* (2021.08); *A61N 2005/007* (2013.01); *A61N 2005/0644* (2013.01)

(58) Field of Classification Search
  CPC . A61B 18/20; A61B 18/201; A61B 2018/202; A61B 18/203; A61B 2018/2035; A61B 18/22; A61B 2018/225; A61B 2018/2255; A61N 2005/007; A61N 5/0616; A61N 5/0617; A61N 5/0621; A61N 5/0624; A61N 2005/0644; A61N 5/067
  USPC .................. 606/9–11, 20, 22–23; 607/88–90
  See application file for complete search history.

(56) References Cited

U.S. PATENT DOCUMENTS

| | | | | |
|---|---|---|---|---|
| 5,814,040 A | * | 9/1998 | Nelson | A61B 18/0218 606/2 |
| 6,059,820 A | * | 5/2000 | Baronov | A61B 18/02 606/9 |
| 6,451,007 B1 | * | 9/2002 | Koop | A61B 18/20 606/7 |
| 2008/0119828 A1 | * | 5/2008 | Nelson | A61B 18/203 606/9 |
| 2008/0200908 A1 | * | 8/2008 | Domankevitz | A61B 18/203 606/9 |
| 2020/0337771 A1 | * | 10/2020 | Schomacker | A61N 5/0616 |

(Continued)

FOREIGN PATENT DOCUMENTS

| | | |
|---|---|---|
| JP | 2001514057 A | 9/2001 |
| KR | 10-2004-0101967 A | 12/2004 |
| KR | 10-1015881 B1 | 2/2011 |

(Continued)

*Primary Examiner* — Ahmed M Farah
(74) *Attorney, Agent, or Firm* — NKL Law; Byungwoong Park

(57) ABSTRACT

The provided is a handpiece for skin laser treatment and a medical laser treatment apparatus including the same. The disclosed handpiece for skin laser treatment may include a handpiece body including a laser irradiation portion for irradiating a laser beam to a treatment target area of the skin of a person to be treated and a refrigerant spraying portion for spraying a refrigerant in the treatment target area; and an end tool member provided at an end of the handpiece body and configured to maintain a distance between the laser irradiation portion and the skin in contact with the skin of the person to be treated and to at least partially limit a target area corresponding to the treatment target area.

12 Claims, 19 Drawing Sheets

(56) References Cited

U.S. PATENT DOCUMENTS

2023/0086046 A1* 3/2023 Kim .................. F25B 13/00
 62/132

FOREIGN PATENT DOCUMENTS

| | | |
|---|---|---|
| KR | 10-2015-0026704 A | 3/2015 |
| KR | 10-2017-0003488 A | 1/2017 |
| WO | WO-0071044 A1 * 11/2000 | ........... A61B 18/203 |

* cited by examiner

HANDPIECE FOR SKIN LASER TREATMENT AND MEDICAL LASER TREATMENT APPARATUS INCLUDING THE SAME

CROSS-REFERENCE TO RELATED APPLICATION(S)

This application claims priority from and the benefit of Korean Patent Application No. 10-2023-0006892 filed on Jan. 17, 2023, which is hereby incorporated by reference in its entirety.

BACKGROUND

1. Field

The present invention relates to a handle-type device and an apparatus including the same, and more particularly, to a handpiece for skin laser treatment and a medical laser treatment apparatus including the same.

2. Related Art

A $CO_2$ laser device is widely used for skin procedure/treatment. The $CO_2$ laser device refers to a device that generates a laser (i.e., $CO_2$ laser) using carbon dioxide ($CO_2$) as a medium. A wavelength of $CO_2$ laser may be 10600 nm. The $CO_2$ laser has high water absorption and generates high thermal energy. Such $CO_2$ laser is highly effective in treatment of scar and acne and skin regeneration, compared to other lasers.

Skin treatment using the $CO_2$ laser uses the principle that, when the $CO_2$ laser is irradiated to the skin containing a large amount of water, the moisture in the skin tissue is vaporized and evaporated and the skin is scraped off or the skin tissue is burned. The $CO_2$ laser may irradiate the laser at an accurate position due to less reflection or scattering, may minimize destruction of normal tissue and easily destroy only the lesion tissue, may have relatively less pain and swelling after treatment, and may have a less chance of post-infection after treatment since the laser itself has sterilizing power. The $CO_2$ laser may be used for dermabrasion, removal of facial wrinkles, removal of chicken pox and pimple marks, and removal and treatment of moles, freckles, age spots, epidermal hair follicles, acne scars, scars after surgery or trauma, skin tags (ductile fibroma), warts, corns, and other skin lesions/abnormal tissue and tumor.

However, the $CO_2$ laser generates high temperature and strong heat compared to other lasers, which may cause severe pain to a patient. Therefore, in general, procedure may be performed after several tens of minutes (e.g., about 30 minutes) after local anesthetic is applied, or after partial or general anesthetic is applied with an anesthetic injection. Therefore, there are issues, such as delay in the procedure due to anesthesia, increased burden on medical staff, and anxiety and burden of the patient. To solve such issues, an attempt is being made to apply a method of cooling the skin using cooling gas or cooling water to the $CO_2$ laser device as a substitute for anesthesia.

However, since the $CO_2$ laser device performs continuous and fast laser irradiation within a narrow range, it is not easy to implement technology for spraying refrigerant right before laser oscillation. Also, since a laser irradiation speed does not catch up with a refrigerant spray speed, a gap between the laser irradiation range and the refrigerant spray range is highly likely to occur. Also, when irradiating laser, there is a need to appropriately adjust a spray direction and a spray area of refrigerant in proportion to an energy amount and area of the irradiated laser. However, development of technology related thereto is still incomplete.

In the case of spraying too much refrigerant, when $CO_2$ laser is irradiated, it may be hindered due to water absorption that is a unique characteristic of the $CO_2$ laser. That is, due to an excessive amount of refrigerant, the procedure using the laser may not be properly performed. Also, due to excessive refrigerant spray, refrigerant consumption may increase. If the refrigerant is irradiated for a relatively long period of time, temperature of the skin surface may significantly decrease, which may lead to reducing a treatment effect or energy efficiency. Meanwhile, if a spray amount of refrigerant is too small, it may be difficult to achieve the purpose of alleviating pain of a patient during laser irradiation. Also, when performing skin treatment using laser, there may be various modes related to laser irradiation and the laser may be irradiated in various ways for various skin lesions or abnormal tissues. Therefore, there is a need to develop technology for appropriately adjusting a range (area), a direction, an Angle, and a flow rate (i.e., spray intensity) of refrigerant spray according to the intention of a user (operator) based on a mode and a method related to the laser irradiation. The range (area), the direction, the angle, and the flow rate (i.e., spray intensity) of refrigerant spray may have a close correlation with characteristics of the procedure (good or bad) and reduction in a patient's pain. Here, it may be difficult to achieve the intention and purpose of the user (operator) simply by spraying refrigerant.

Patent document includes Korean Patent Registration NO. 10-1015881.

SUMMARY

A technical subject to be achieved by the present invention is to provide a handpiece for skin laser treatment that may improve a procedure characteristic and also improve a pain relief effect of a patient (i.e., minimize pain of the patient) by allowing a user (operator) to easily control a spray range (area) of refrigerant according to the intention of the user (operator).

Also, a technical subject to be achieved by the present invention is to provide a handpiece for skin laser treatment that may accomplish an optimal procedure and a cooling effect in various laser treatment methods by easily controlling a spray direction, an angle, a spray amount, and a flow rate (i.e., spray intensity) of refrigerant as well as a spray range of refrigerant.

Also, a technical subject to be achieved by the present invention is to provide a medical laser treatment apparatus including the handpiece.

Subjects to be solved by the present invention are not limited to the aforementioned subjects and still other subjects not described herein may be clearly understood by one of ordinary skill in the art from the following description.

According to an aspect of an example embodiment, there is provided a handpiece for skin laser treatment, the handpiece including a handpiece body including a laser irradiation portion for irradiating a laser beam to a treatment target area of the skin of a person to be treated and a refrigerant spraying portion for spraying a refrigerant in the treatment target area; and an end tool member provided at an end of the handpiece body and configured to maintain a distance between the laser irradiation portion and the skin in contact with the skin of the person to be treated and to at least partially limit a target area corresponding to the treatment target area, wherein the refrigerant spraying portion includes a refrigerant spray nozzle having a refrigerant outlet for discharging the refrigerant toward the target area; and a nozzle positioning member configured to connect to the refrigerant spray nozzle and to adjust a distance between the refrigerant spray nozzle and the target area by changing a position of the refrigerant spray nozzle, and the range of the refrigerant that is sprayed to the skin of the person to be treated is configured to be controllable by adjusting the distance between the refrigerant spray nozzle and the target area using the nozzle positioning member.

The refrigerant spray nozzle may have a first hollow hole through which the refrigerant passes and a first spiral portion may be provided on an inner surface of the first hollow hole, the nozzle positioning member may have a second hollow hole through which the refrigerant passes through communication with the first hollow hole, the nozzle positioning member may include a threaded insertion portion configured to insert into the first hollow hole and to couple with the refrigerant spray nozzle and having a second spiral portion engaged with the first spiral portion on its outer circumferential surface and an adjustment head provided at an upper end of the threaded insertion portion. The distance between the refrigerant spray nozzle and the target area may be adjusted by rotating the adjustment head.

The handpiece may further include a fixing member configured to prevent rotation of the refrigerant spray nozzle on the outer surface of the refrigerant spray nozzle and to allow linear displacement in a longitudinal direction of the refrigerant spray nozzle.

The refrigerant spray nozzle may further include a spray amount adjustment unit for adjusting a spray amount of the refrigerant, and a size of the refrigerant outlet may be controlled by the spray amount adjustment unit.

The spray amount adjustment unit may include an opening limiting member configured to limit an opening area and having a plurality of guide grooves formed around the opening area; a plurality of outlet adjustment plates configured to couple with the opening limiting member, and provided to be in contact with each other to define the refrigerant outlet with respect to the opening area and to connect to the plurality of guide grooves, respectively; and a rotatable control member configured to move the plurality of outlet adjustment plates along the plurality of guide grooves. A size of the refrigerant outlet may be controlled by moving the plurality of outlet adjustment plates along the plurality of guide grooves using the rotatable control member.

Each of the plurality of outlet adjustment plates may have a fan shape or a triangular shape, each of the plurality of guide grooves may have an arc-shaped structure or a rectilinear structure, and each of the plurality of guide grooves may have one end closer to the opening area than the other end and may be formed to be farther from the opening area toward the other end.

The rotatable control member may be controlled in a manual manner.

The rotatable control member may be controlled in an electrical manner.

The refrigerant spraying portion may be configured to spray the refrigerant in a direction that forms an angle of about 20° to 45° relative to an irradiation direction of the laser beam.

The handpiece for skin laser treatment may further include a tilting device configured to tilt the refrigerant spraying portion. A spray direction of the refrigerant may be controlled by tilting the refrigerant spraying portion using the tilting device.

The laser irradiation portion may be configured to irradiate a $CO_2$ laser beam.

According to another aspect of an example embodiment, there is provided a medical laser treatment apparatus including the aforementioned handpiece.

The medical laser treatment apparatus may include a device body configured to connect to the handpiece; and a connecting arm configured to connect between the device body and the handpiece, and the device body may include a laser generator configured to generate the laser beam and a refrigerant supply configured to supply the refrigerant.

According to some example embodiments, it is possible to implement a handpiece for skin laser treatment that may improve a procedure characteristic and also improve a pain relief effect of a patient (i.e., minimize pain of the patient) by allowing a user (operator) to easily control a spray range (area) of refrigerant according to the intention of the user (operator). Also, according to some example embodiments, it is possible to implement a handpiece for skin laser treatment that may accomplish an optimal procedure and a cooling effect in various laser treatment methods by easily controlling a spray direction, an angle, a spray amount, and a flowrate (i.e., spray intensity) of the refrigerant as well as a spray range of refrigerant. It is possible to implement a medical laser treatment apparatus having excellent performance and control functions by applying the handpiece according to the example embodiment.

In the case of using a handpiece and medical laser treatment apparatus according to an example embodiment, it is possible to reduce a procedure time and cost and to lower work intensity of an operator.

In the case of using a handpiece and a medical laser treatment apparatus according to an example embodiment, it is possible to reduce pain of a patient by easily and precisely adjusting an area of refrigerant spray.

In the case of using a handpiece and a medical laser treatment apparatus according to an example embodiment, it is possible to prevent refrigerant from being unnecessarily sprayed in an area outside a procedure and to reduce the occurrence of risk, such as frostbite, caused by direct contact between the refrigerant and the skin from over spraying.

In the case of using a handpiece and a medical laser treatment apparatus according to an example embodiment, it is possible to improve the problem of reduced treatment effectiveness due to the water absorption of the laser and to use laser energy more efficiently by implementing the maximum efficiency of refrigerant in an appropriate amount according to a procedure.

In the case of using a handpiece and a medical laser treatment apparatus according to an example embodiment, it is possible to save refrigerant being unnecessarily wasted, to improve economic feasibility, and to enhance environmental issues by accurately spraying the refrigerant only in a targeted spot area in which laser is irradiated through adjustment of a spray amount and spray range of the refrigerant.

However, the effects of the present invention are not limited to the aforementioned effects and may be variously expanded without departing from the technical spirit and scope of the present invention.

BRIEF DESCRIPTION OF THE FIGURES

Various aspects are described with reference to the accompanying drawings and, herein, like reference numerals refer to like elements throughout. In the following example embodiments, numerous specific details are set forth herein to provide thorough understanding of at least one aspect for the purpose of explanation. However, it will be apparent that such aspect(s) may be practiced without the specific details. In other examples, known structures and devices are illustrated in a form of a block diagram to easily describe at least one aspect.

DETAILED DESCRIPTION

Figure 1:
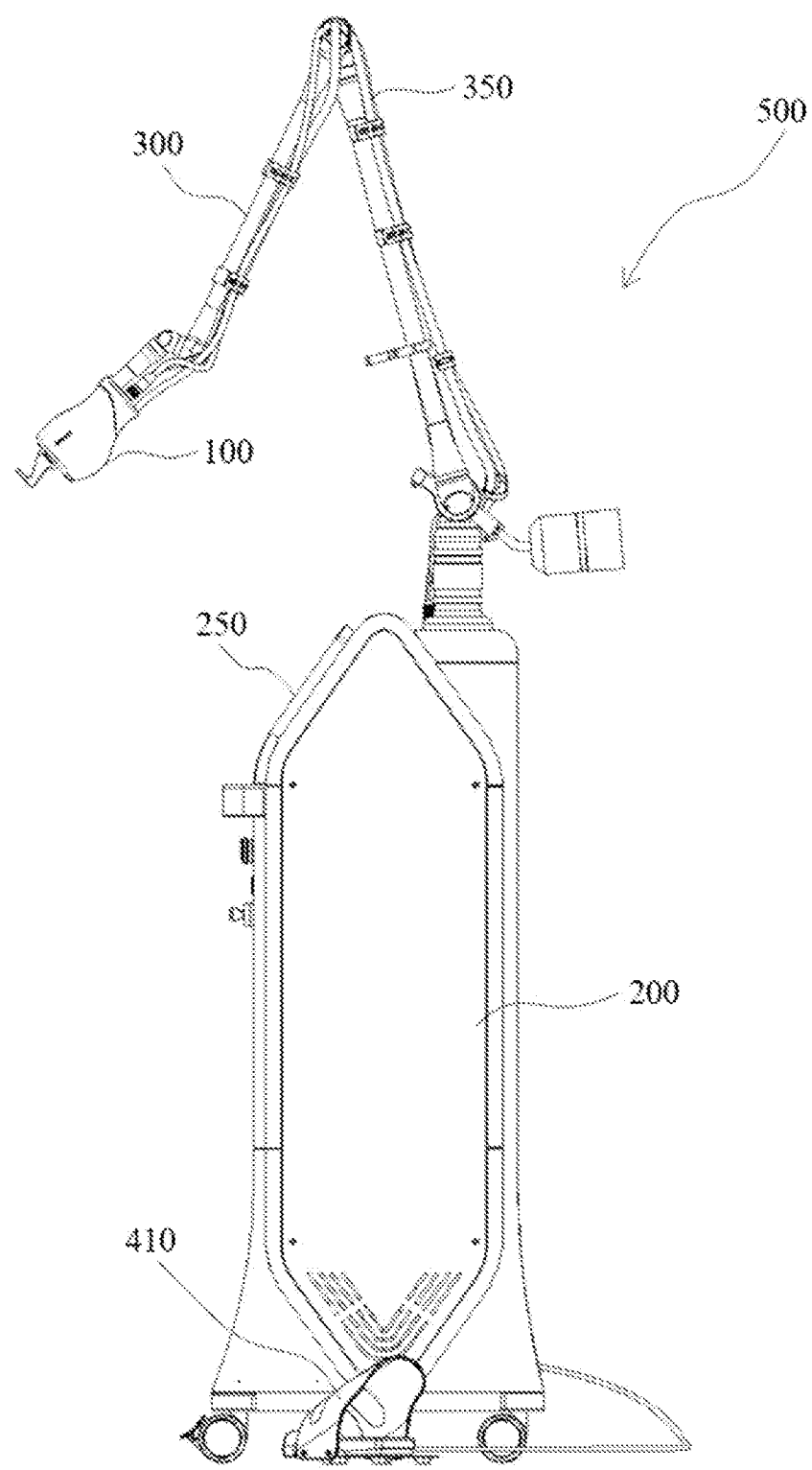
FIG. 1 is a perspective view illustrating a medical laser treatment apparatus including a handpiece for skin laser treatment according to an example embodiment.

Hereinafter, example embodiments will be described with reference to the accompanying drawings.

The following example embodiments are provided to clearly explain the present invention to one of ordinary skills in the art and the scope of the present invention is not limited to the example embodiments and the example embodiments may be modified in various forms.

The terms used herein are used to simply explain specific example embodiments and are not construed to limit the present invention. Singular forms "a," "an," and "the," are intended to include the plural forms as well, unless the context clearly indicates otherwise. It will be further understood that the terms "comprises/comprising (incudes/including)" when used in this specification, specify the presence of stated features, integers, steps, operations, elements, and/or components, but do not preclude the presence or addition of one or more other features, integers, steps, operations, elements, components, and/or groups, thereof. Also, the term "connect" used herein may include that some components are directly connected and also that another component is further provided between components and indirectly connected accordingly.

In addition, when it is described that one component is located "on" another component, it indicates that a component is in contact with the other component and also still another component is present between two components. As used herein, the term "and/or" includes any one and all combinations of one or more associated items. Also, the terms of degree, such as "about" and "substantially," are used to indicate a range of or close to that the number or degree taking into consideration of inherent manufacturing and material tolerance and are used to prevent undue exploitation by an infringer of the stated invention for an exact or absolute number provided to help understanding of the present application.

Hereinafter, example embodiments are described with reference to the accompanying drawings. Sizes or thicknesses of areas or parts shown in the accompanying drawings may be slightly exaggerated for clarity of specification and convenience of description. Like reference numerals refer to like elements throughout.

FIG. 1 is a perspective view illustrating a medical laser treatment apparatus 500 including a handpiece 100 for skin laser treatment according to an example embodiment.

Referring to FIG. 1, the medical laser treatment apparatus 500 according to an example embodiment may include the handpiece 100, a device body 200 configured to connect to the handpiece 100, and a connecting arm 300 configured to connect between the device body 200 and the handpiece 100. The connecting arm 300 may be a mechanical arm member having multiple joints. The handpiece 100 is held by an operator by hand to use for procedure/treatment and may include a 'laser irradiation portion' for irradiating a laser beam to a treatment target area of the skin of a person to be treated and a 'refrigerant spraying portion' for spraying refrigerant to the treatment target area. A specific structure and characteristic of the handpiece 100 will be further described with reference to FIGS. 2 to 10.

The device body 200 may include a 'laser generator' configured to generate the laser beam and a 'refrigerant supply' configured to supply the refrigerant. The laser beam generated by the laser generator of the device body 200 may be transmitted to the laser irradiation portion of the handpiece 100 and may be irradiated from the laser irradiation portion to the skin of the person to be treated. The refrigerant may be supplied from the refrigerant supply of the device body 200 to the refrigerant spraying portion of the handpiece 100 and may be sprayed from the refrigerant spraying portion to the skin of the person to be treated.

Here, the refrigerant may represent a cooling fluid and the cooling fluid may include cooling gas. For example, the refrigerant may include gas such as compressed freon gas. However, a type of the refrigerant disclosed herein is provided as an example only and may be variously modified depending on cases.

The laser beam may be, for example, a $CO_2$ laser beam. In this case, the laser irradiation portion of the handpiece 100 may be configured to irradiate the $CO_2$ laser beam. The $CO_2$ laser beam (i.e., $CO_2$ laser) may have, for example, a wavelength of 10600 nm. The $CO_2$ laser has high water absorption and generates high thermal energy. Compared to other lasers, such $CO_2$ laser may exhibit excellent performance and effect in terms of scar and acne treatment and skin regeneration. The $CO_2$ laser may be usefully used for dermabrasion, removal of facial wrinkles, removal of chicken pox and pimple marks, and removal and treatment of moles, freckles, age spots, epidermal hair follicles, acne scars, scars after surgery or trauma, skin tags (ductile fibroma), warts, corns, and other skin lesions/abnormal tissue and tumor. However, in an example embodiment, the laser beam is not limited to the $CO_2$ laser and other types of lasers may be used depending on cases.

The medical laser treatment apparatus 500 may include at least one connecting member 350 connected between the device body 200 and the handpiece 100. The connecting member 350 may be provided along the connecting arm 300 and may be coupled to the connecting arm 300. For example, the connecting member 350 may include at least one of a cable, a tube (hose), and an electrical wire. Here, the tube (hose) may be a member for transmitting (supplying) refrigerant.

According to an example embodiment, the medical laser treatment apparatus 500 may further include a control device unit 250. For example, although the control device unit 250 may be installed on a top surface of the device body 200, a position thereof may be variously modified. For example, the control device unit 250 may include a touchpad-type display device and the touchpad-type display device may include a microprocessor as a kind of a computer device. A user (operator) may set a laser irradiation mode, a laser irradiation condition, a refrigerant spray mode, and a refrigerant spray condition using the control device unit 250, and may control the overall driving condition of the medical laser treatment apparatus 500.

According to an example embodiment, a first manipulation unit for controlling a laser beam irradiation operation may be provided to the handpiece 100. The first manipulation unit may have various structures, such as a button, a switch, and an adjustment wheel structure. The user (operator) may control the laser beam irradiation operation depending on necessity using the first manipulation unit. Also, a second manipulation unit for controlling a refrigerant spray operation may be further provided to the handpiece 100. The second manipulation unit may have various structures, such as a button, a switch, and an adjustment wheel structure. The user (operator) may control the refrigerant spray operation depending on necessity using the second manipulation unit.

According to an example embodiment, the medical laser treatment apparatus 500 may further include a pedal-type manipulation unit 410. For example, the pedal-type manipulation unit 410 may relate to controlling the refrigerant spray operation. The user (operator) may control the refrigerant spray operation in the handpiece 100 by manipulating the pedal-type manipulation unit 410 using a foot of the user. In the case of using the pedal-type manipulation unit 410, the refrigerant spray operation may be more easily controlled. However, the pedal-type manipulation unit 410 may be optionally used. Additionally, for convenience of movement, a plurality of wheel units (casters) may be further provided in a lower portion of the device body 200.

Figure 2:
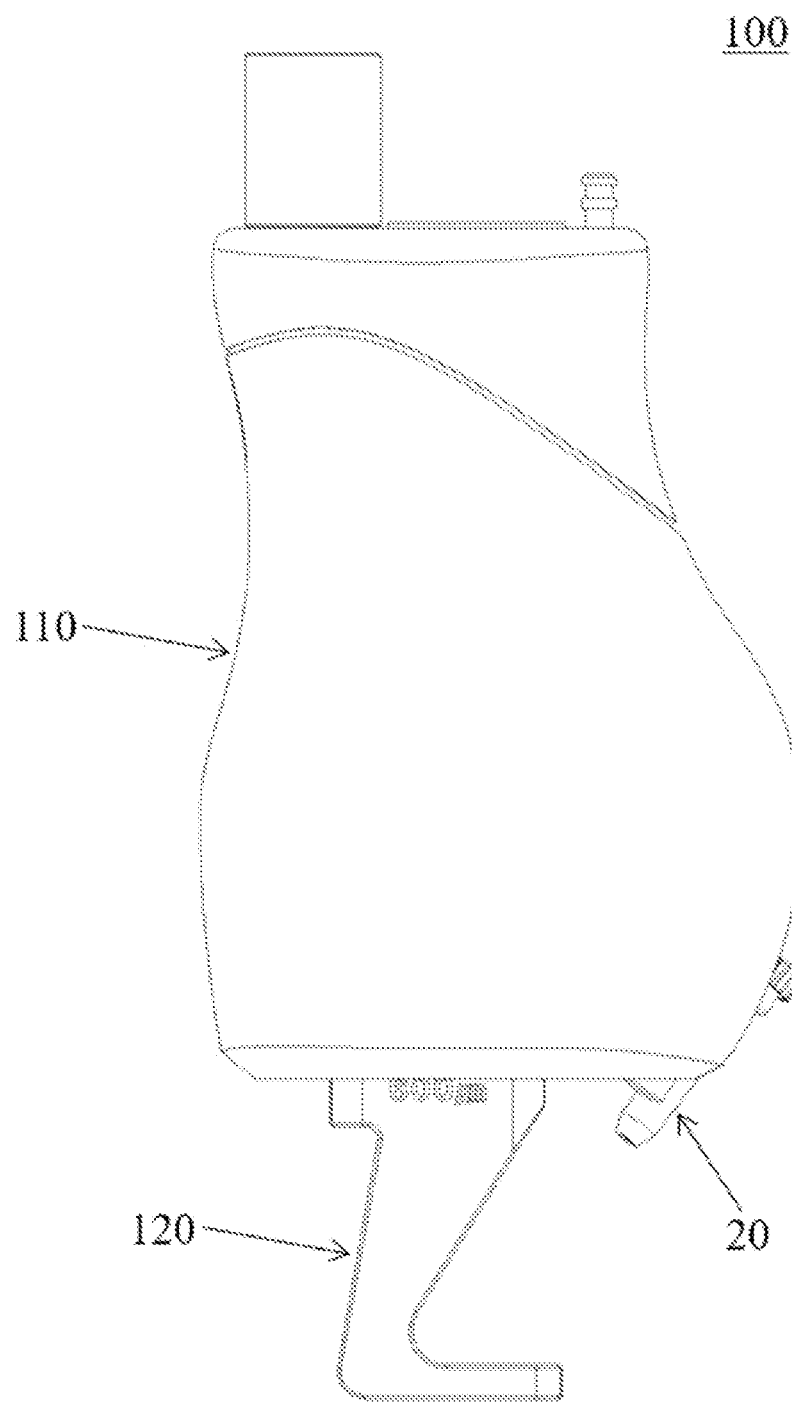
FIGS. 2 to 4 illustrate a handpiece for skin laser treatment according to an example embodiment.
Figure 3:
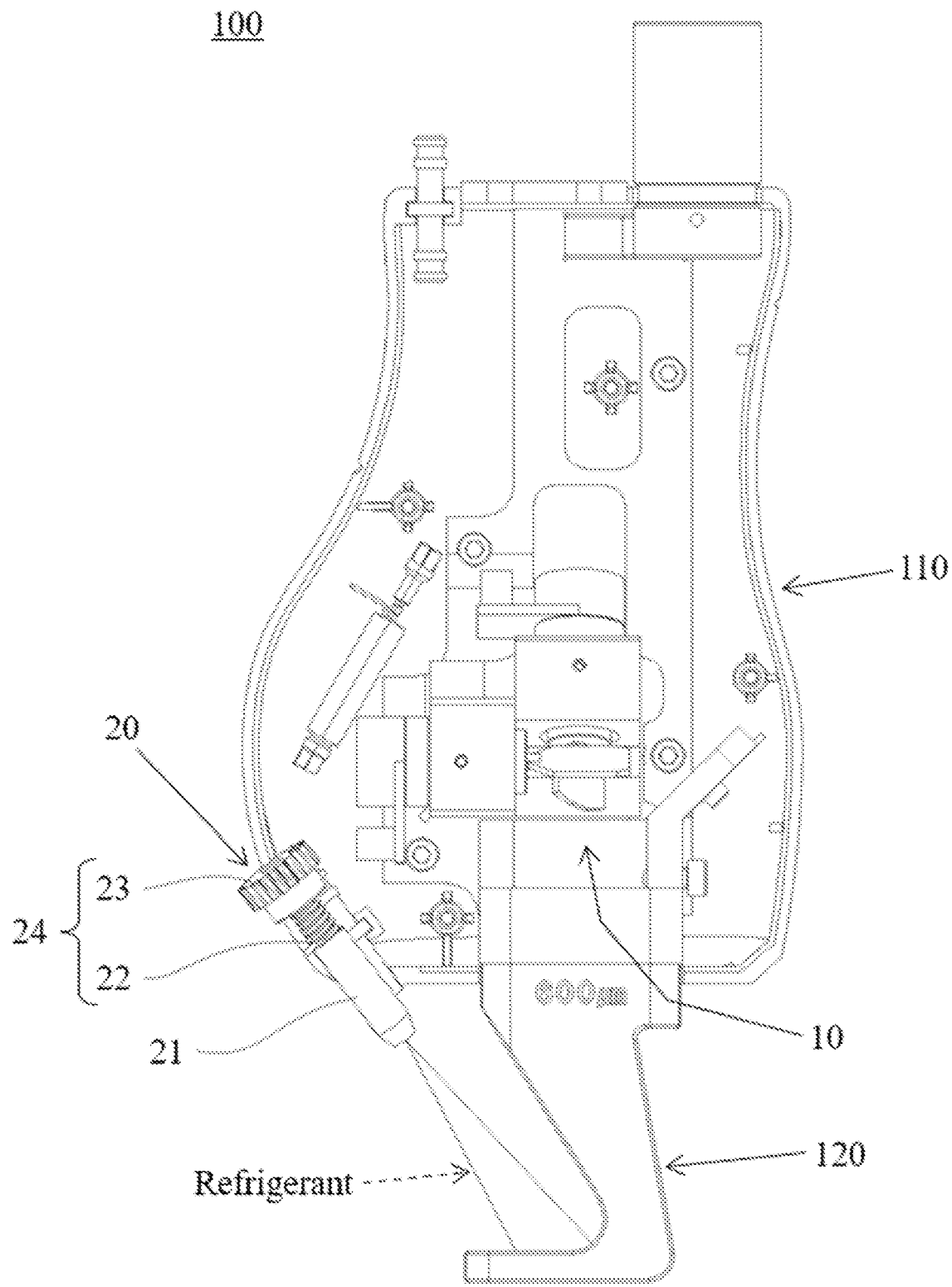
Figure 4:
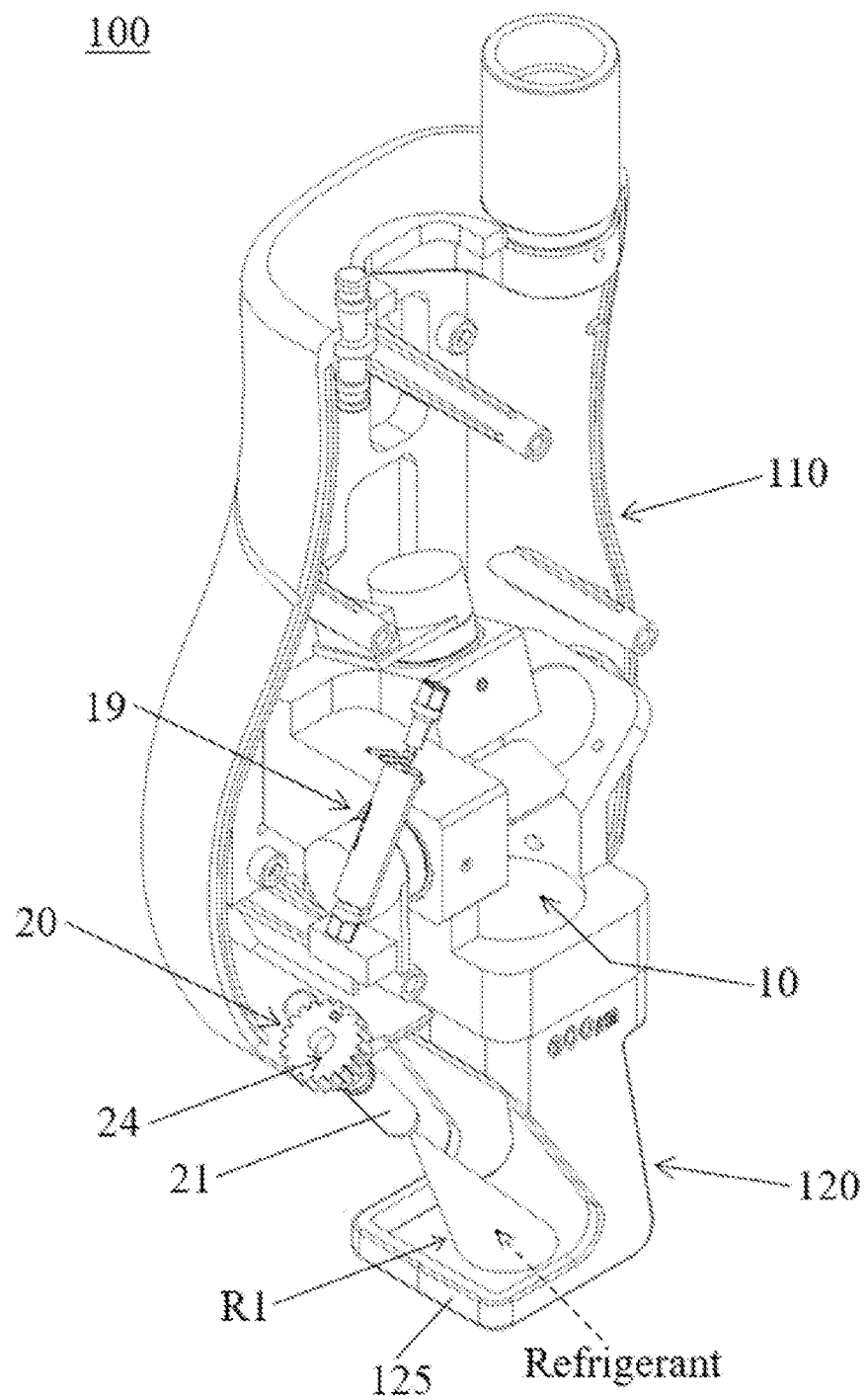

FIGS. 2 to 4 illustrate a handpiece 100 for skin laser treatment according to an example embodiment. FIG. 2 is a side view of the handpiece 100, FIG. 3 is an internal side view lustrating an internal configuration of the handpiece 100, and FIG. 4 is a perspective view illustrating an internal configuration of the handpiece 100.

Referring to FIGS. 2 to 4, the handpiece 100 for skin laser treatment according to an example embodiment may include a handpiece body 110 and an end tool member 120 provided at an end of the handpiece body 110.

The handpiece body 110 refers to a portion that is held by an operator by hand to use for procedure and may include a laser irradiation portion 10 for irradiating a laser beam to a treatment target area of the skin of a person to be treated and a refrigerant spraying portion 20 for spraying a refrigerant to the treatment target area. The end tool member 120 is provided at the end (i.e., end of a lower portion) of the handpiece body 110 and may serve to maintain a distance between the laser irradiation portion 10 and a skin contact portion 127 of the end tool member 120 in contact with the skin of the person to be treated and may be configured to at least partially limit a target area (R1) corresponding to the treatment target area. The end tool member 120 may include a frame unit 125 configured to at least partially surround the target area (R1) corresponding to the treatment target area. The frame unit 125 may have a form that defines an open area for exposing the target area (R1) and a lower end of the frame unit 125 may contact the skin of the person to be treated. However, a detailed structure of the end tool member 120 may be variously modified without being limited thereto.

The laser irradiation portion 10 may include an optical system through which the laser beam passes and an emitting portion through which the laser beam is emitted. The laser beam transmitted by a laser transmission member may be emitted through the emitting portion by passing through the optical system. The laser beam emitted through the emitting portion may be irradiated to the target area (R1). The laser beam may be irradiated in a direction parallel (or a direction substantially parallel) to a longitudinal direction of the handpiece 100 (height in the drawings). Referring to FIGS. 2 to 4, the laser beam may be irradiated to the target area (R1) in a vertical direction (or substantially vertical direction). However, an irradiation direction of the laser beam may vary depending on cases.

If the laser beam is a $CO_2$ laser beam, it is possible to generate minutely distributed fractional beams by splitting a single laser beam into a plurality of beams using a special optical lens and a motor in the handpiece 100 and to irradiate the fractional beams to the skin, distributing heat to a relatively wide skin tissue area and reducing damage by high temperature of the laser. The fractional beam may be generated in various forms/shapes through electronic control by mathematical calculation. For example, the fractional beam may be implemented in a circular shape, a quadrangular shape, a rhombus shape, an oval shape, a square shape, or a rectangular shape according to the intention of a user (operator), and may produce weak or strong energy through single or overlapping irradiation using a time difference in each dot (i.e., laser spot). Also, when implementing the fractional beam in various shapes/forms, energy (i.e., fluence) of the laser may be adjusted weakly or strongly according to the intention of the user (operator). In the case of using the fractional beam, effective procedure may be performed using various methods while reducing damage to other skin tissues.

The refrigerant spraying portion 20 may include a refrigerant spray nozzle 21 and a nozzle positioning member 24 connected thereto. The refrigerant spray nozzle 21 may have a refrigerant outlet for discharging the refrigerant toward the target area (R1). The refrigerant may be discharged from the refrigerant outlet and may be sprayed to the target area (R1). The nozzle positioning member 24 may be a member for adjusting a distance between the refrigerant spray nozzle 21 and the target area (R1) by changing a position of the refrigerant spray nozzle 21. The spray range of the refrigerant to the skin of the person to be treated may be adjusted by adjusting the distance between the refrigerant spray nozzle 21 and the target area (R1) using the nozzle positioning member 24. When the distance between the refrigerant spray nozzle 21 and the target area (R1) is set to be short by the nozzle positioning member 24, the range (area) in which the refrigerant is sprayed to the skin may be relatively narrowed. Conversely, when the distance between the refrigerant spray nozzle 21 and the target area (R1) is set to be long by the nozzle positioning member 24, the range (area) in which the refrigerant is sprayed to the skin may be relatively widened. Therefore, according to the intention of the user (operator), the range in which the refrigerant is sprayed to the skin of the person to be treated may be easily and precisely adjusted.

According to an example embodiment, referring to FIG. 3, the nozzle positioning member 24 may include a threaded insertion portion 22 configured to couple with the refrigerant spray nozzle 21 and an adjustment head 23 provided at an upper end of the threaded insertion portion 22. The threaded insertion portion 22 and the adjustment head 23 may be provided in an integral structure. A distance between the refrigerant spray nozzle 21 and the target area (R1 of FIG. 4) may be adjusted by rotating the adjustment head 23. According to a direction of rotation of the adjustment head 23, the refrigerant spray nozzle 21 may move closer to or farther from the target area (R1 of FIG. 4). Rotation of the adjustment head 23 may be controlled in a manual manner, but may also be controlled in an electrical manner if necessary. Therefore, the distance between the refrigerant spray nozzle 21 and the target area (R1 of FIG. 4) may be controlled manually or automatically (electrically).

A refrigerant supply tube (hose) (not shown) configured to connect to the refrigerant spraying portion 20 may be further provided. The refrigerant supply tube may be connected to the adjustment head 23, and the refrigerant supplied from the refrigerant supply tube may pass through the inside of the nozzle positioning member 24 and may be discharged (sprayed) from the refrigerant outlet of the refrigerant spray nozzle 21. Also, a refrigerant solenoid valve 19 may be further provided inside the handpiece body 110, and the refrigerant solenoid valve 19 may be connected to the refrigerant spraying portion 20 through a predetermined tube (hose) member. Also, the refrigerant solenoid valve 19 may be connected to the refrigerant supply of the aforementioned device body (200 of FIG. 1) through a predetermined connecting method. The refrigerant solenoid valve 19 may be electrically controlled.

The refrigerant solenoid valve 19 may be in an ON state or an OFF state. For example, when the refrigerant solenoid valve 19 is in the ON state, an outlet of the refrigerant solenoid valve 19 may be opened and the refrigerant may be transmitted from the refrigerant solenoid valve 19 to the refrigerant spraying portion 20. When the refrigerant solenoid valve 19 is in the OFF state, the outlet of the refrigerant solenoid valve 19 may be closed and the refrigerant may not be transmitted from the refrigerant solenoid valve 19 to the refrigerant spraying portion 20.

Figure 5:
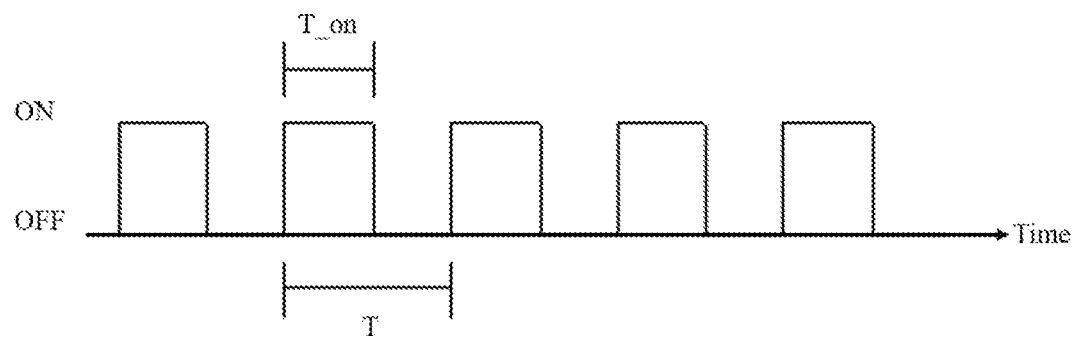
FIG. 5 is a graph showing a change in an ON/OFF state of a refrigerant solenoid valve according to an example embodiment.

FIG. 5 is a graph showing a change in an ON/OFF state of the refrigerant solenoid valve 19 according to an example embodiment.

Referring to FIG. 5, a change in the ON/OFF state of the refrigerant solenoid valve 19 may be represented as a pulse waveform. The medical laser treatment apparatus 500 may adjust a refrigerant spray time by adjusting a time period (T) of pulse waveform and a duration time (T_on) of the ON state in the pulse waveform. The medical laser treatment apparatus 500 may adjust a refrigerant spray amount by adjusting the refrigerant spray time.

Figure 6A:
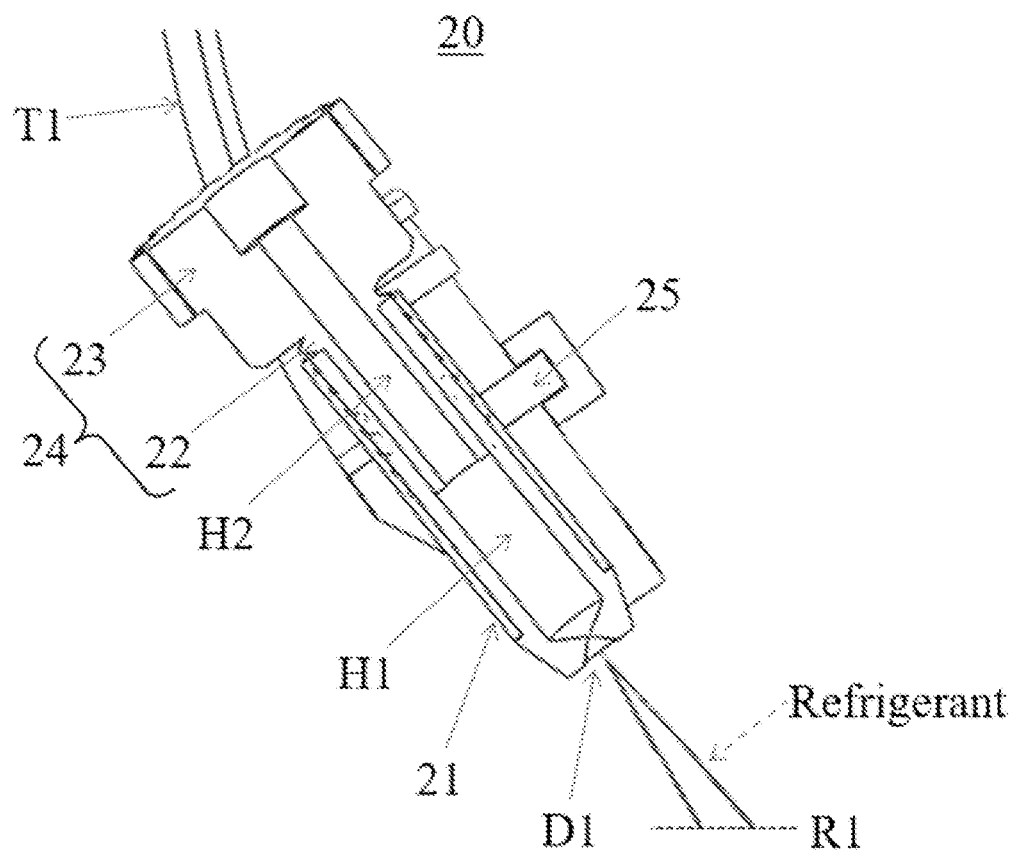
FIGS. 6A and 6B are cross-sectional views for describing a configuration of a refrigerant spraying portion applicable to a handpiece for skin laser treatment and a refrigerant spray range adjustment method using the same according to an example embodiment.
Figure 6B:
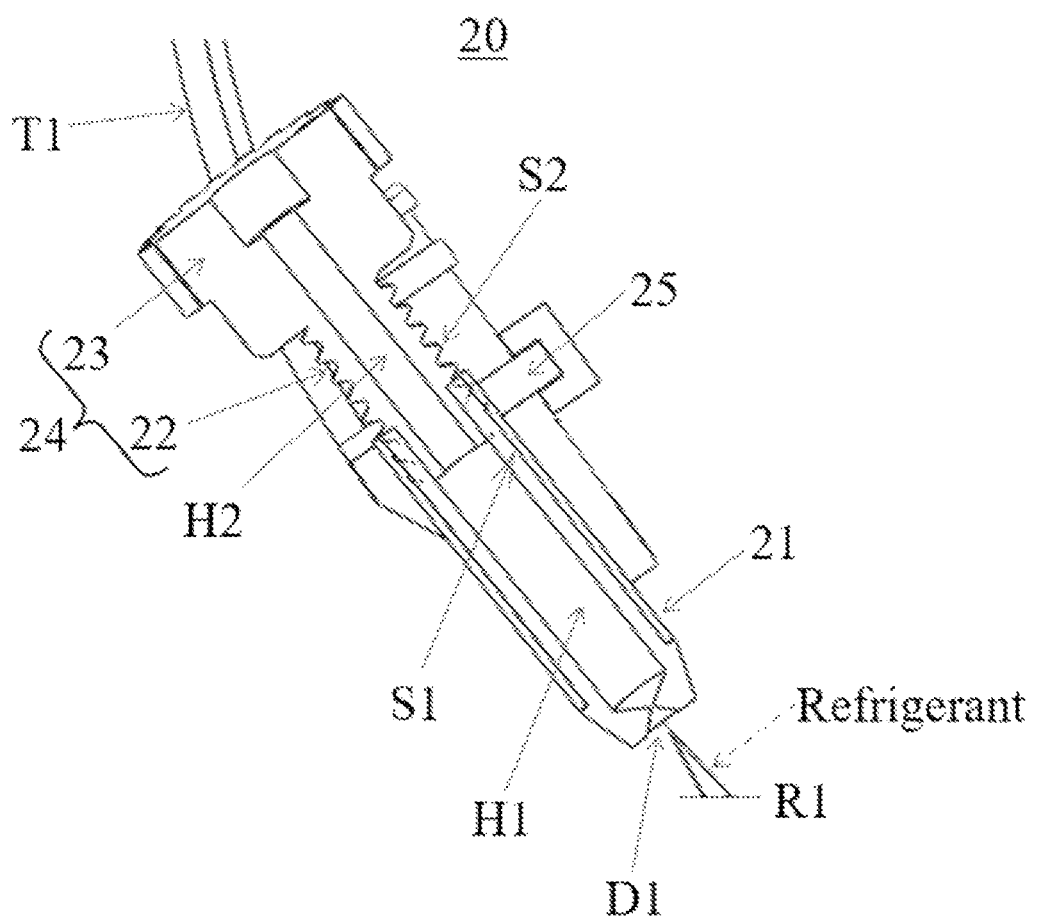

FIGS. 6A and 6B are cross-sectional views for describing a configuration of a refrigerant spraying portion 20 applicable to a handpiece for skin laser treatment and a refrigerant spray range adjustment method using the same according to an example embodiment. FIG. 6A illustrates a case in which a distance between a refrigerant spray nozzle 21 and a target area (R1) is set to be relatively long, and FIG. 6B illustrates a case in which the distance between the refrigerant spray nozzle 21 and the target area (R1) is set to be relatively short.

Referring to FIGS. 6A and 6B, the refrigerant spraying portion 20 may include the refrigerant spray nozzle 21 and a nozzle positioning member 24 connected thereto. The refrigerant spray nozzle 21 may have a refrigerant outlet (D1) for discharging the refrigerant toward the target area (R1). The refrigerant may be discharged from the refrigerant outlet (D1) and may be sprayed to the target area (R1). The nozzle positioning member 24 may be a member for adjusting a distance between the refrigerant spray nozzle 21 and the target area (R1) by changing a position of the refrigerant spray nozzle 21.

The refrigerant spray nozzle 21 may have, for example, an approximately elongated cylindrical structure. The refrigerant spray nozzle 21 may have a first hollow hole (H1) through which the refrigerant passes and a first spiral portion (S1) may be provided on an inner surface of the first hollow hole (H1). The nozzle positioning member 24 may have, for example, a screw structure having a head or a structure similar thereto. The nozzle positioning member 24 may have a second hollow hole (H2) through which the refrigerant passes through communication with the first hollow hole (H1). The nozzle positioning member 24 may include a threaded insertion portion 22 configured to insert into the first hollow hole (H1) and to couple with the refrigerant spray nozzle 21 and having a second spiral portion(S2) engaged with the first spiral portion (S1) on its outer circumferential surface and an adjustment head 23 provided at an upper end of the threaded insertion portion 22. The second hollow hole (H2) may be formed by passing through the adjustment head 23 and the threaded insertion portion 22. A refrigerant supply tube (hose) (Ti) configured to connect to the refrigerant spraying portion 20 may be further provided. The refrigerant supply tube (Ti) may be connected to a second hollow hole (H2) portion of the adjustment head 23 and the refrigerant supplied from the refrigerant supply tube (Ti) may pass through the second hollow hole (H2) and the first hollow hole (H1) and may be discharged (sprayed) through the refrigerant outlet (D1).

The range in which the refrigerant is sprayed to the skin of the person to be treated may be adjusted by adjusting the distance between the refrigerant spray nozzle 21 and the target area (R1) using the nozzle positioning member 24. As illustrated in FIG. 6A, when the distance between the refrigerant spray nozzle 21 and the target area (R1) is set to be long by the nozzle positioning member 24, the range (area) in which the refrigerant is sprayed to the skin may be relatively widened. As illustrated in FIG. 6B, When the distance between the refrigerant spray nozzle 21 and the target area (R1) is set to be short by the nozzle positioning member 24, the range (area) in which the refrigerant is sprayed to the skin may be relatively narrowed.

The distance between the refrigerant spray nozzle 21 and the target area (R1) may be adjusted by rotating the adjustment head 23. According to a direction of rotation of the adjustment head 23, the refrigerant spray nozzle 21 may move closer to or farther from the target area (R1). According to an example embodiment, a fixing member 25 may be further provided on an outer surface of the refrigerant spray nozzle 21. The fixing member 25 may be configured to prevent rotation of the refrigerant spray nozzle 21 and to allow linear displacement in a longitudinal direction of the refrigerant spray nozzle 21. For example, a groove in the longitudinal direction of the refrigerant spray nozzle 21 may be formed on the outer surface of the refrigerant spray nozzle 21 and an end of the fixing member 25 may insert into the groove. In this case, rotation of the refrigerant spray nozzle 21 may be prevented by the fixing member 25 and the linear displacement in the longitudinal direction of the refrigerant spray nozzle 21 may be allowed. Therefore, in response to rotating the adjustment head 23, a position of the refrigerant spray nozzle 21 may be farther from or closer to the adjustment head 23 according to the direction of the rotation. The fixing member 25 may be regarded as a portion of the nozzle positioning member 24. That is, the fixing member 25 may be regarded to be included in the nozzle positioning member 24. Also, the fixing member 25 may be regarded to be included in the refrigerant spraying portion 20. However, a detailed configuration of the refrigerant spraying portion 20 and a refrigerant spray range adjustment method described above with reference to FIGS. 6A and 6B are provided as an example only and may be modified depending on cases.

Figure 7:
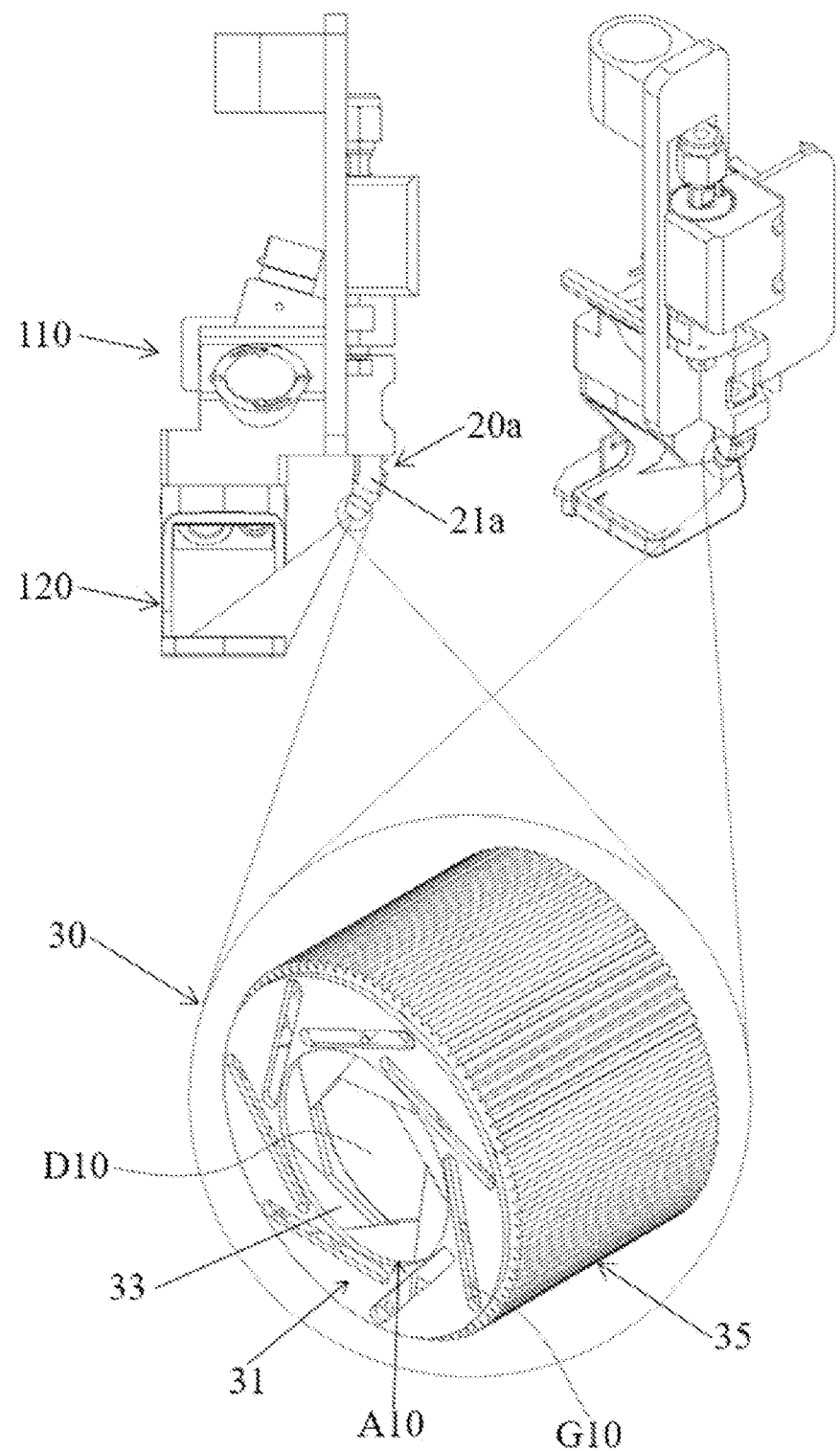
FIGS. 7 and 8 are perspective views illustrating a handpiece for skin laser treatment according to another example embodiment.
Figure 8:
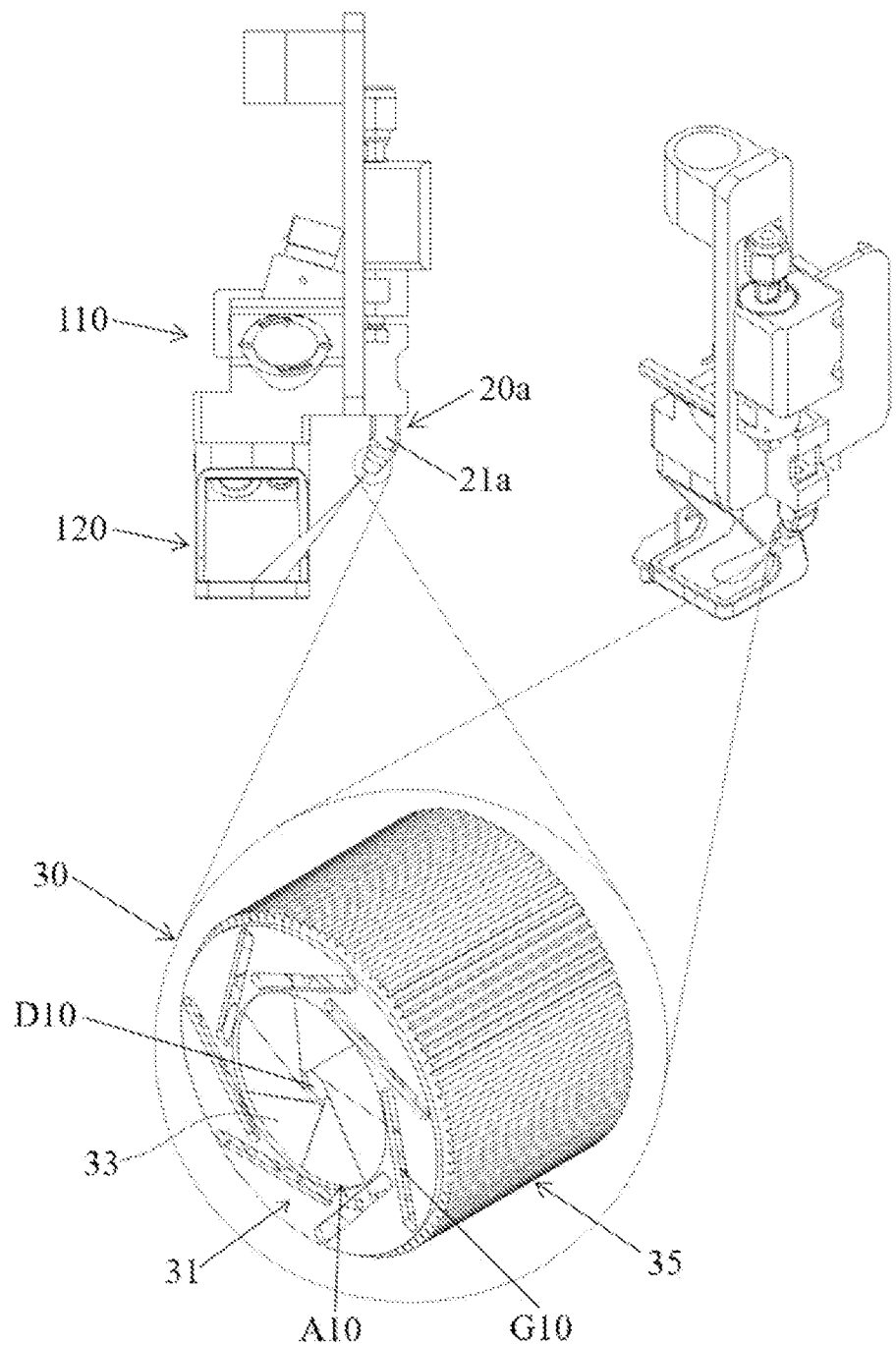

FIGS. 7 and 8 are perspective views illustrating a handpiece for skin laser treatment according to another example embodiment.

Referring to FIGS. 7 and 8, the handpiece according to the example embodiment may include a refrigerant spraying portion 20a. The refrigerant spraying portion 20a may include a refrigerant spray nozzle 21a. The refrigerant spray nozzle 21a may include a spray amount adjustment unit 30 for adjusting a refrigerant spray amount at its end (lower end). A size of a refrigerant outlet (D10) may be controlled by the spray amount adjustment unit 30. FIG. 7 illustrates a case in which the refrigerant outlet (D10) is relatively widened by the spray amount adjustment unit 30 and FIG. 8 illustrates a case in which the refrigerant outlet (D10) is relatively narrowed by the spray amount adjustment unit 30.

According to an example embodiment, the spray amount adjustment unit 30 may include an opening limiting member 31, a plurality of outlet adjustment plates 33, and a rotatable control member 35. The opening limiting member 31 may limit an opening area (A10) and have a plurality of guide grooves (G10) formed around the opening area (A10). The plurality of guide grooves (G10) may be guide holes. The plurality of outlet adjustment plates 33 may couple with the opening limiting member 31. The plurality of outlet adjustment plates 33 may couple with a rear surface portion (inner surface) of the opening limiting member 31. The plurality of outlet adjustment plates 33 may be provided to be in contact with each other to define the refrigerant outlet (D10) with respect to the opening area (A10) and to connect to the plurality of guide grooves (G10), respectively. The rotatable control member 35 may be a member configured to move the plurality of outlet adjustment plates 33 along the plurality of guide grooves (G10). The rotatable control member 35 may have a cylindrical structure, or a structure similar thereto, and may have a sawtooth portion or an unevenness portion along its outer circumferential surface.

The size of the refrigerant outlet (D10) may be controlled by moving the plurality of outlet adjustment plates 33 along the plurality of guide grooves (G10) using the rotatable control member 35. According to a direction of rotation of the rotatable control member 35, the size of the refrigerant outlet (D10) may be enlarged or reduced. According to the size of the refrigerant outlet (D10), a spray amount of refrigerant discharged (sprayed) through the refrigerant outlet (D10) may be adjusted. Therefore, an operator may easily and precisely adjust the refrigerant spray amount according to the intention of the operator. The refrigerant spray amount may be appropriately adjusted according to a type of procedure, a laser irradiation method (mode), and a laser irradiation area.

Control (rotation) of the rotatable control member 35 may be performed in a manual manner. Alternatively, control (rotation) of the rotatable control member 35 may be performed in an electrical manner. In the case of controlling the rotatable control member 35 in an electrical manner, a gear portion (not shown) configured to engage with the rotatable control member 35 may be provided on an outer circumferential surface of the rotatable control member 35 and rotation of the rotatable control member 35 may be controlled by controlling rotation of the gear portion using a motor.

A remaining configuration excluding a configuration in which the refrigerant spray nozzle 21a further includes the spray amount adjustment unit 30 in FIGS. 7 and 8 may be the same as or almost similar to the description made above with reference to FIGS. 1 to 6. Therefore, repeated description related to the remaining configuration is omitted.

Figure 9:
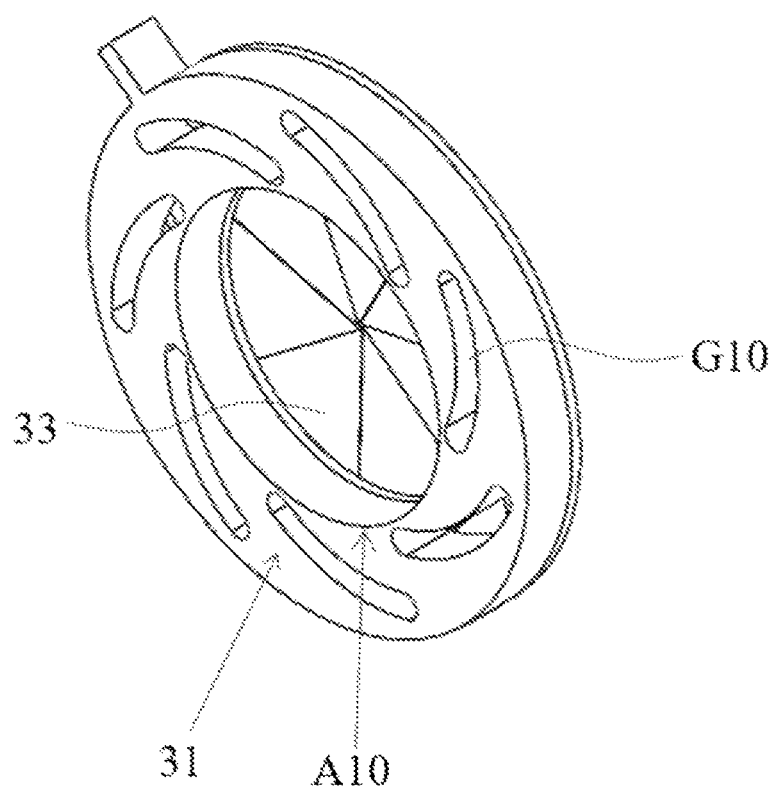
FIG. 9 is a perspective view illustrating an opening limiting member and a plurality of outlet adjustment plates of a spray amount adjustment unit applicable to a handpiece for skin laser treatment according to an example embodiment.

FIG. 9 is a perspective view illustrating an opening limiting member 31 and a plurality of outlet adjustment plates 33 of a spray amount adjustment unit applicable to a handpiece for skin laser treatment according to an example embodiment.

Referring to FIG. 9, as described above, the spray amount adjustment unit may include the opening limiting member 31 and the plurality of outlet adjustment plates 33. The opening limiting member 31 may have a plurality of guide grooves (G10) formed around an opening area (A10) while limiting the opening area (A10). The opening area (A10) may be in a circular shape and each of the plurality of guide grooves (G10) may have an arc-shaped structure or a rectilinear structure. The opening limiting member 31 may have an annular structure as a whole. The plurality of outlet adjustment plates 33 may couple with the opening limiting member 31. The plurality of outlet adjustment plates 33 may couple with a rear surface (inner surface) of the opening limiting member 31. The plurality of outlet adjustment plates 33 may be provided to be in contact with each other to define a refrigerant outlet (D10 of FIGS. 7 and 8) with respect to the opening area (A10) and may be provided to connect to the plurality of guide grooves (G10), respectively.

Figure 10A:
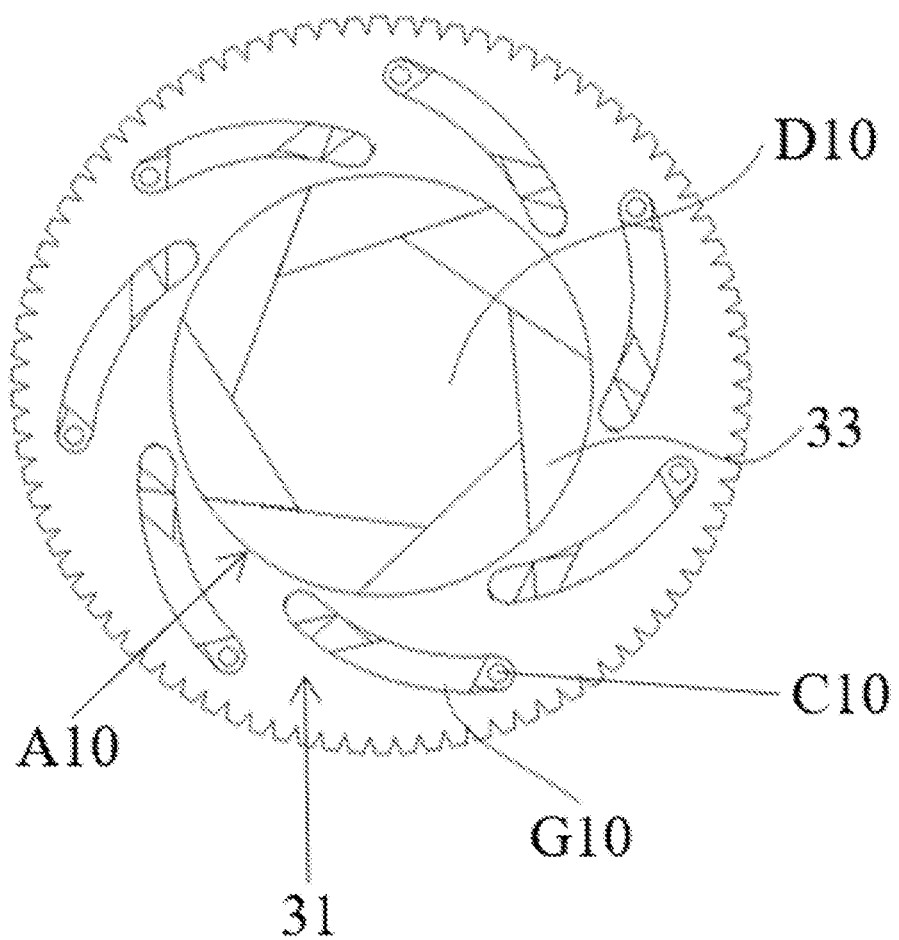
FIGS. 10A and 10B are top views illustrating an opening limiting member and a plurality of outlet adjustment plates of a spray amount adjustment unit applicable to a handpiece for skin laser treatment according to an example embodiment.
Figure 10B:
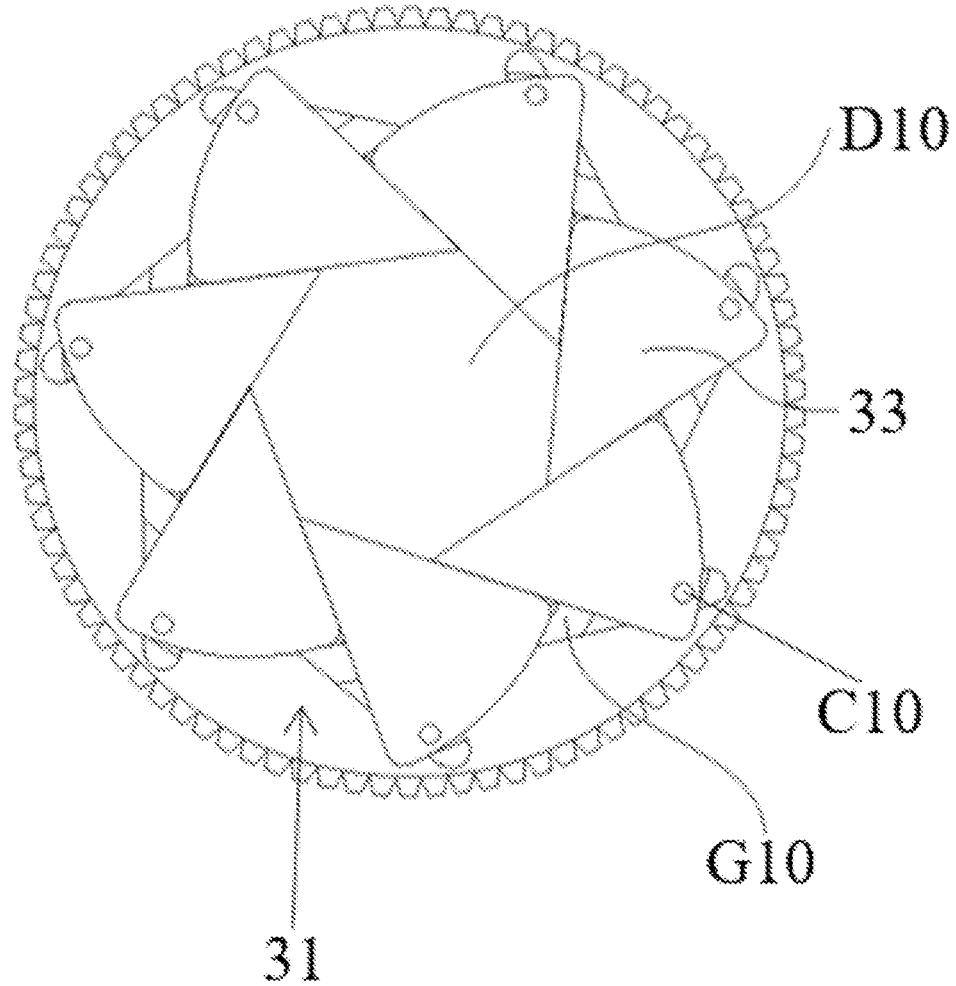

FIGS. 10A and 10B are top views illustrating an opening limiting member 31 and a plurality of outlet adjustment plates 33 of a spray amount adjustment unit applicable to a handpiece for skin laser treatment according to an example embodiment. FIG. 10A shows a front view of the opening limiting member 31 and FIG. 10B shows a rear view of the opening limiting member 31.

Referring to FIGS. 10A and 10B, each of the plurality of outlet adjustment plates 33 may have a fan shape or a triangular shape. Each of the plurality of outlet adjustment plates 33 may be provided such that both sides (two linear sides) come into contact with a side (linear side) of its adjacent outlet adjustment plate 33. As the outlet adjustment plates 33 slidably move in a state in which sides of the adjacent outlet adjustment plates 33 are in contact with each other, a size of the refrigerant outlet (D10) may be adjusted.

Each of a plurality of guide grooves (G10) may have an arc-shaped structure or a rectilinear structure. Also, each of the plurality of guide grooves (G10) may have one end closer to an opening area (A10) than the other end and may be formed to be farther from the opening area (A10) toward the other end. The plurality of guide grooves (G10) may be formed to all rotate in the same direction. For example, when viewed from the front, each of the guide grooves (G10) may be formed to move away from the opening area (A10) in a counterclockwise direction.

The plurality of outlet adjustment plates 33 may be arranged in connection (fastening) to the plurality of guide grooves (G10), respectively. Reference numeral C10 represents a connecting element (fastening element) that connects (fastens) the outlet adjustment plate 33 to the corresponding guide groove (G10). As described above, the size of the refrigerant outlet (D10) may be controlled by moving the plurality of outlet adjustment plates 33 along the plurality of guide grooves (G10).

In the case of using the spray amount adjustment unit 30 described above with reference to FIGS. 7 to 10, it is possible to easily and precisely control a spray amount of refrigerant.

In the case of performing skin treatment using a handpiece for skin laser treatment according to an example embodiment, a method of irradiating a laser beam and a method of spraying refrigerant may be variously modified and adjusted. In particular, the range (area) in which the refrigerant is sprayed or a spray amount of refrigerant may be appropriately adjusted according to the method of irradiating the laser beam and intensity of laser beam.

Figure 11A:
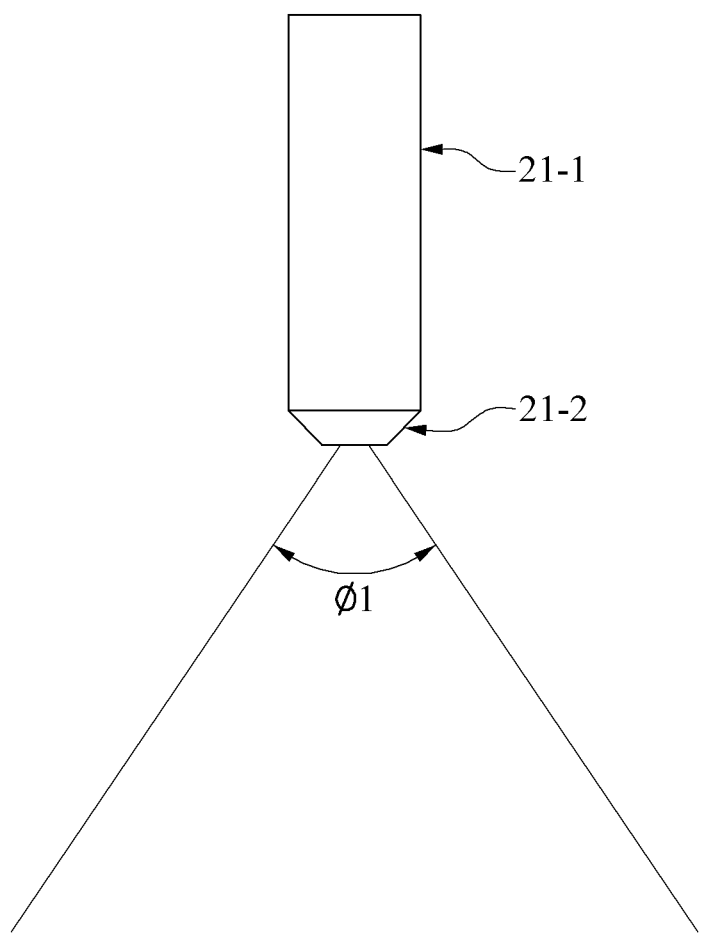
FIGS. 11A and 11B illustrate a change in a spray range angle of refrigerant according to an example embodiment.
Figure 11B:
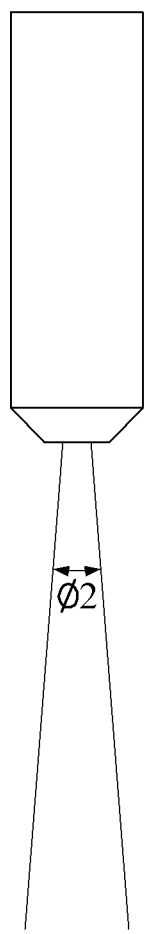

Also, according to an example embodiment, a spray range angle of refrigerant sprayed from a refrigerant spray nozzle 21 may be adjusted. FIGS. 11A and 11B illustrate a change in the spray range angle of refrigerant according to an example embodiment.

As described above, in response to a change in a size or a shape of a refrigerant outlet provided at an end of the refrigerant spray nozzle 21, the spray range angle of refrigerant may change. For example, when the refrigerant needs to be irradiated in a large area, a spray range angle (Ø1) of the refrigerant may be relatively large as illustrated in FIG. 11A. Also, when the refrigerant needs to be irradiated in a narrow area, a spray range angle (Ø2) of refrigerant may become relatively small, such that a spray shape of refrigerant may approach a straight line as illustrated in FIG. 11B.

Also, as illustrated in FIGS. 11A and 11B, the refrigerant spray nozzle 21 may include a nozzle body 21-1 and a nozzle tip 21-2 configured to couple at an end of the nozzle body 21-1. The spray range angle of refrigerant and spray amount of refrigerant may also be changed due to replacement of the nozzle tip 21-2.

Figure 12:
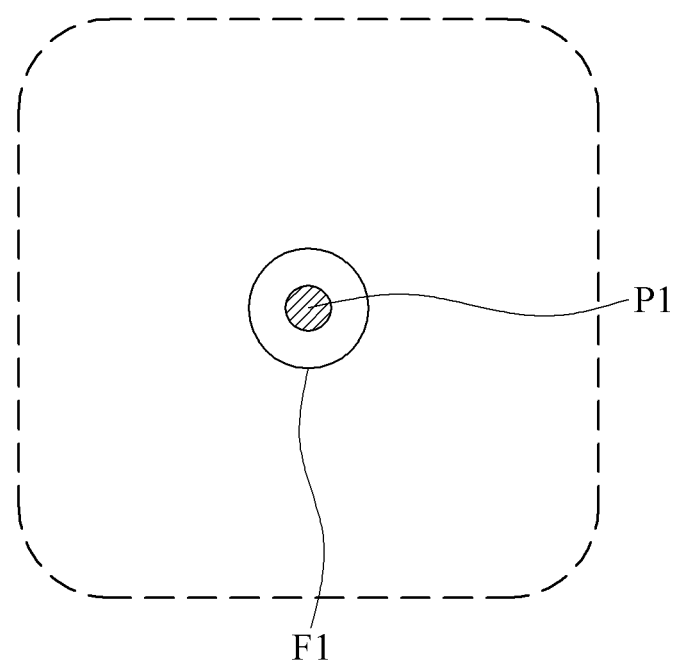
FIGS. 12 and 13 are top views for describing a method of irradiating a laser beam and a method of spraying refrigerant when performing a skin treatment using a handpiece for skin laser treatment according to an example embodiment.
Figure 13:
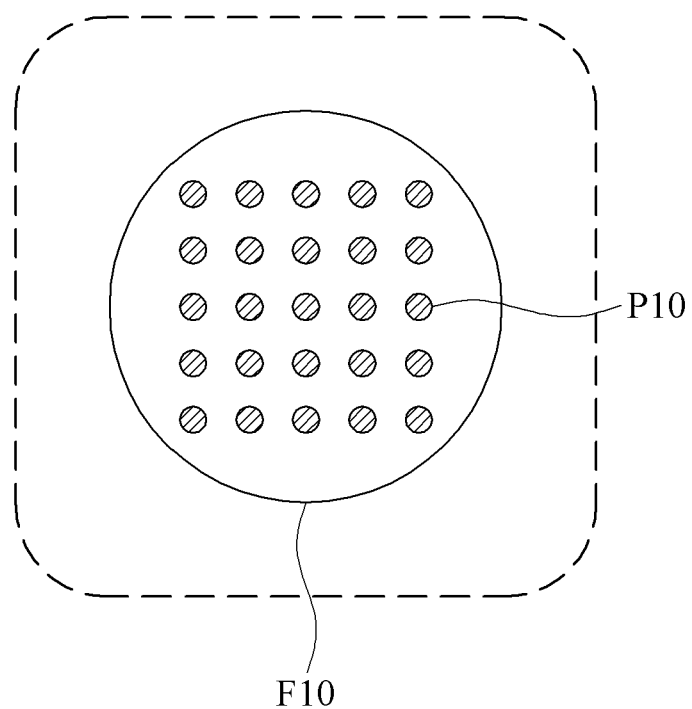

FIGS. 12 and 13 are top views for describing a method of irradiating a laser beam and a method of spraying refrigerant when performing skin treatment using a handpiece for skin laser treatment according to an example embodiment.

Referring to FIG. 12, a laser beam may be irradiated to a single dot (i.e., a laser spot). Reference numeral P1 represents a laser spot to which the laser beam is irradiated. In this case, an area (F1) in which the refrigerant is sprayed may be limited to a surrounding area that includes the laser spot (P1). An appropriate amount of refrigerant may be sprayed within an appropriate range by adjusting a position of a refrigerant spray nozzle and by controlling a spray amount of refrigerant.

Referring to FIG. 13, the laser beam may be irradiated to multiple points in a form of a plurality of split and dispersed fractional beams. Reference numeral P10 represents a plurality of laser spots to which fractional beams are irradiated. Although a distribution form of fractional beams may be variously modified, it is provided as a rectangular shape as an example. The laser beam may be irradiated to the plurality of laser spots (P10) with a slight time difference, or may be irradiated simultaneously or almost simultaneously. An area (F10) in which the refrigerant is sprayed may be a peripheral area that includes the plurality of laser spots (P10). Here, F10 of FIG. 13 may be a wider area than F1 of FIG. 12. Since the range (area) in which the refrigerant is sprayed or a spray amount thereof may be appropriately adjusted according to a method of irradiating a laser beam or intensity of laser beam, procedure may be performed under an optimal condition according to the intention of a user.

The laser beam irradiation method and the refrigerant spray method described above with reference to FIGS. 12 and 13 are provided as an example only and may be variously modified.

Figure 14:
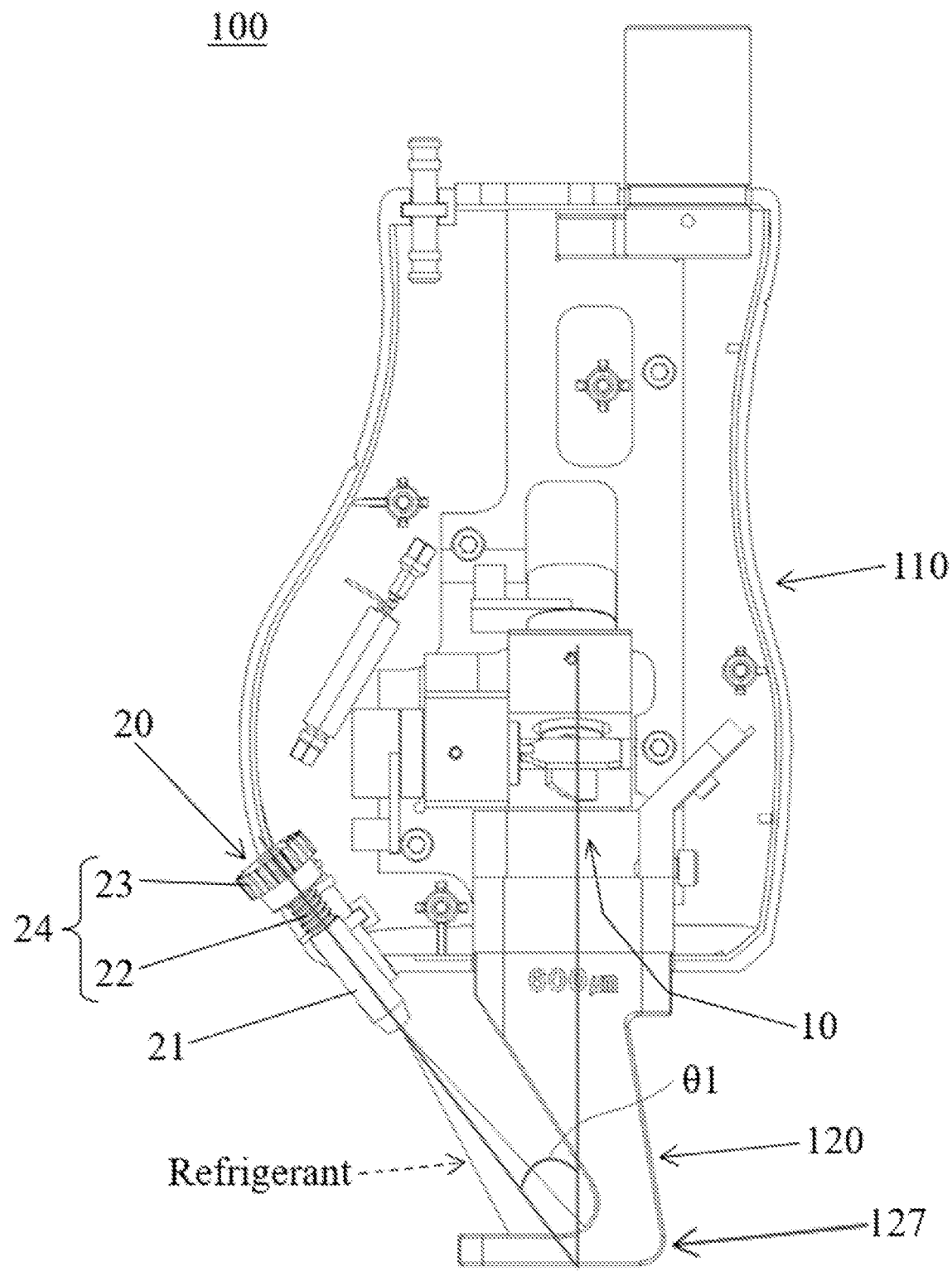
FIG. 14 is a cross-sectional view illustrating a handpiece for skin laser treatment according to an example embodiment.

FIG. 14 is a cross-sectional view illustrating a handpiece 100 for skin laser treatment according to an example embodiment.

Referring to FIG. 14, in the handpiece 100 for skin laser treatment according to the example embodiment, a refrigerant spraying portion 20 may be configured to spray refrigerant in a direction that forms an angle (Ø1) of about 20° to 45° with respect to an irradiation direction of the laser beam. Here, the irradiation direction of the laser beam may be a vertical direction or a substantially vertical direction in the drawings. The spray direction of refrigerant may represent a central direction of refrigerant spraying. When the refrigerant is sprayed under the aforementioned angle condition, procedure may be more easily performed while increasing a cooling effect.

Figure 15:
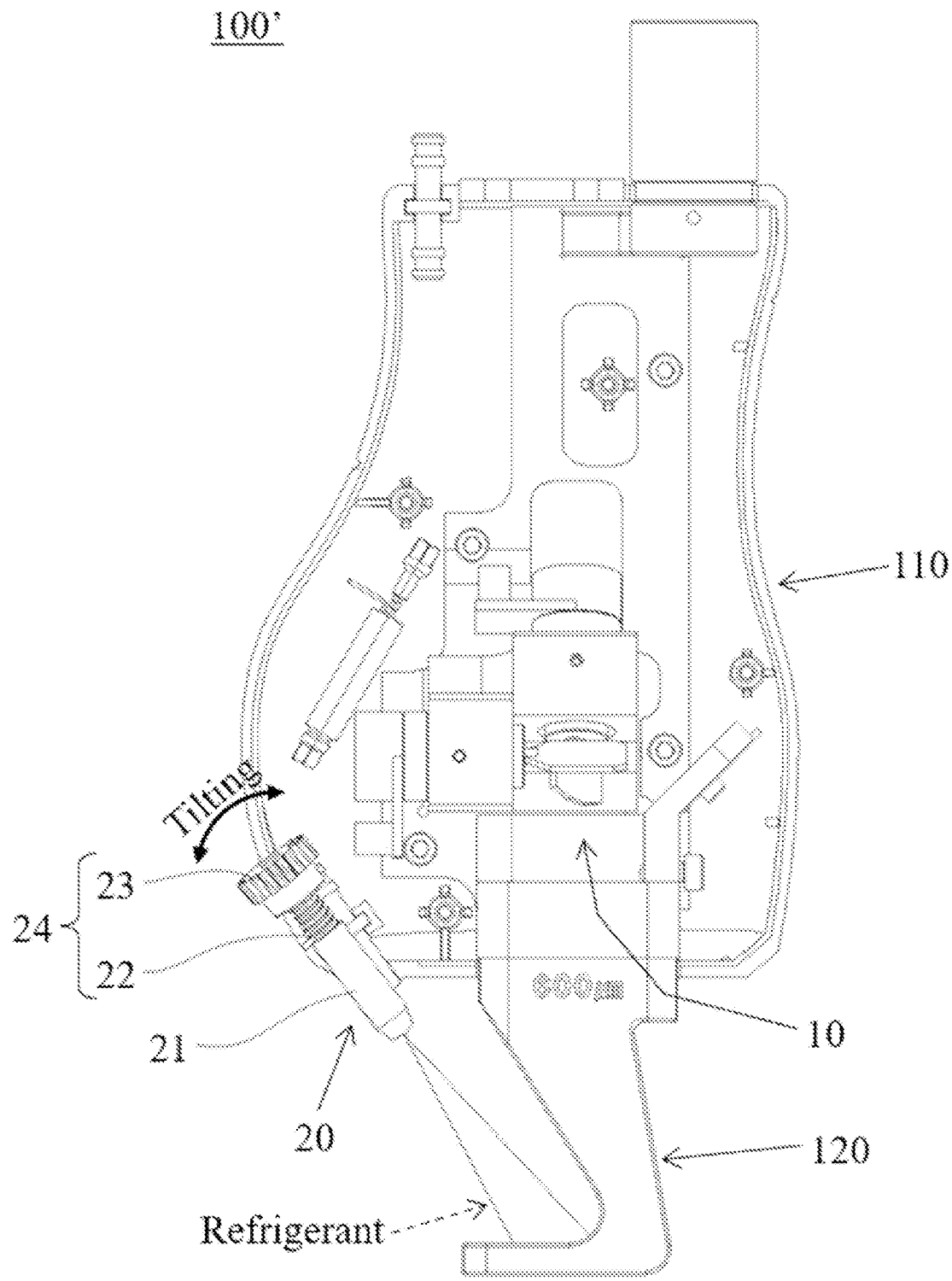
FIG. 15 is a cross-sectional view illustrating a handpiece for skin laser treatment according to another example embodiment.

FIG. 15 is a cross-sectional view illustrating a handpiece 100' for skin laser treatment according to another example embodiment.

Referring to FIG. 15, the handpiece 100' for skin laser treatment according to the example embodiment may further include a 'tilting device' (tilting member) for tilting a refrigerant spraying portion 20. A spray direction of refrigerant may be controlled by tilting the refrigerant spraying portion 20 using the tilting device. Here, titling of the refrigerant spraying portion 20 may be performed while changing the angle θ1 described with FIG. 14 within a predetermined range.

Figure 16:
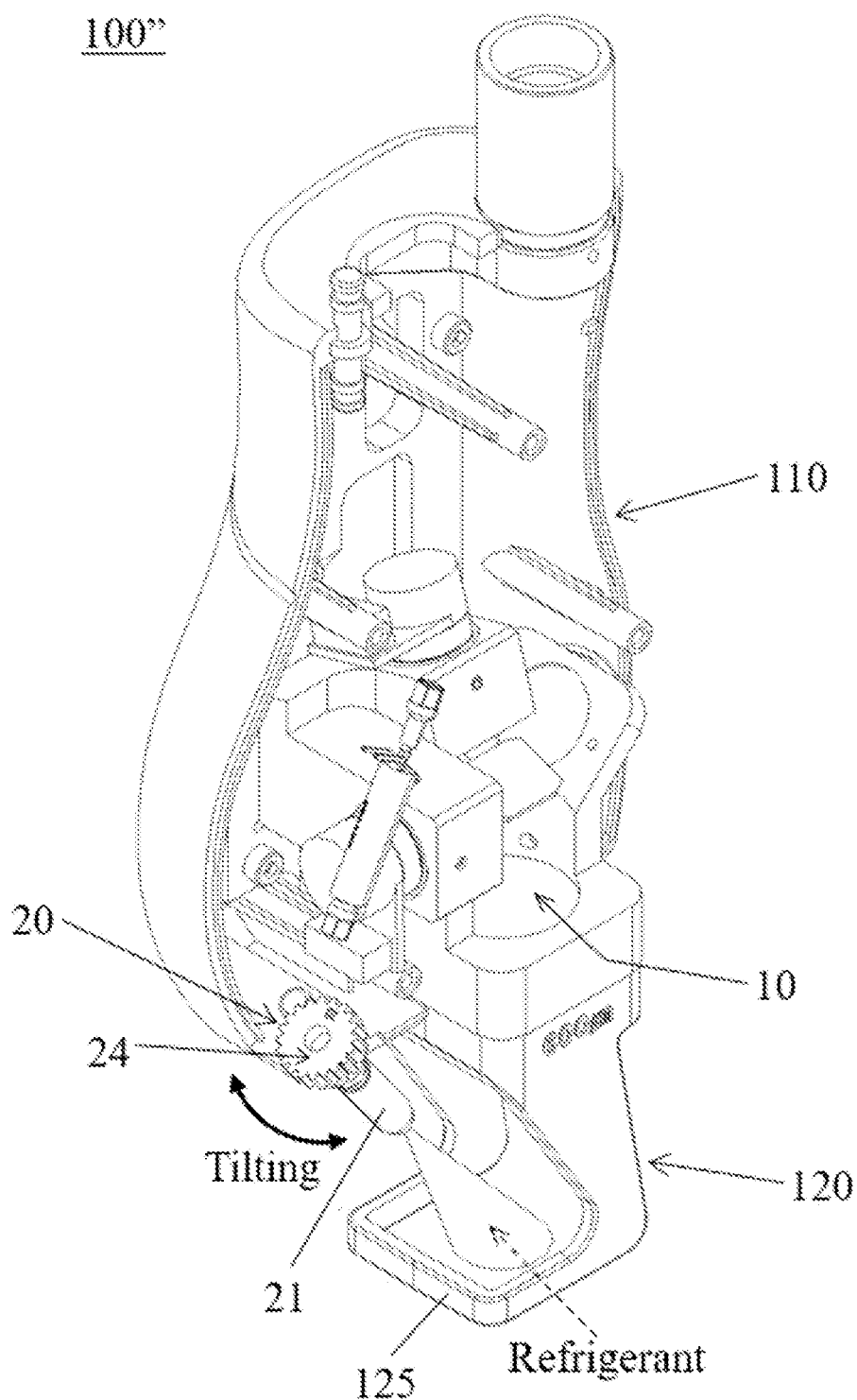
FIG. 16 is a perspective view illustrating a handpiece for skin laser treatment according to another example embodiment.

FIG. 16 is a perspective view illustrating a handpiece 100" for skin laser treatment according to another example embodiment.

Referring to FIG. 16, the handpiece 100" for skin laser treatment according to the example embodiment may further include a 'tilting device' (tilting member) for tilting a refrigerant spraying portion 20. Here, tiling of the refrigerant spraying portion 20 may represent a change of angle or a change of direction in a left-right direction (i.e., a lateral direction). A spray direction of refrigerant may be controlled by tilting the refrigerant spraying portion 20 using the tilting device.

If a refrigerant spray direction is controlled through tilting of the refrigerant spraying portion 20 as illustrated in FIGS. 15 and 16, procedure may be more effectively performed when treating a curved part of the skin or intensively targeting a small area, such as a wart or a mole. Depending on cases, titling methods of FIGS. 15 and 16 may be grafted. Although the tilting device is not illustrated in detail in FIGS. 15 and 16, the tilting device may be implemented using various methods, such as a hinge method or other methods.

Figure 17:
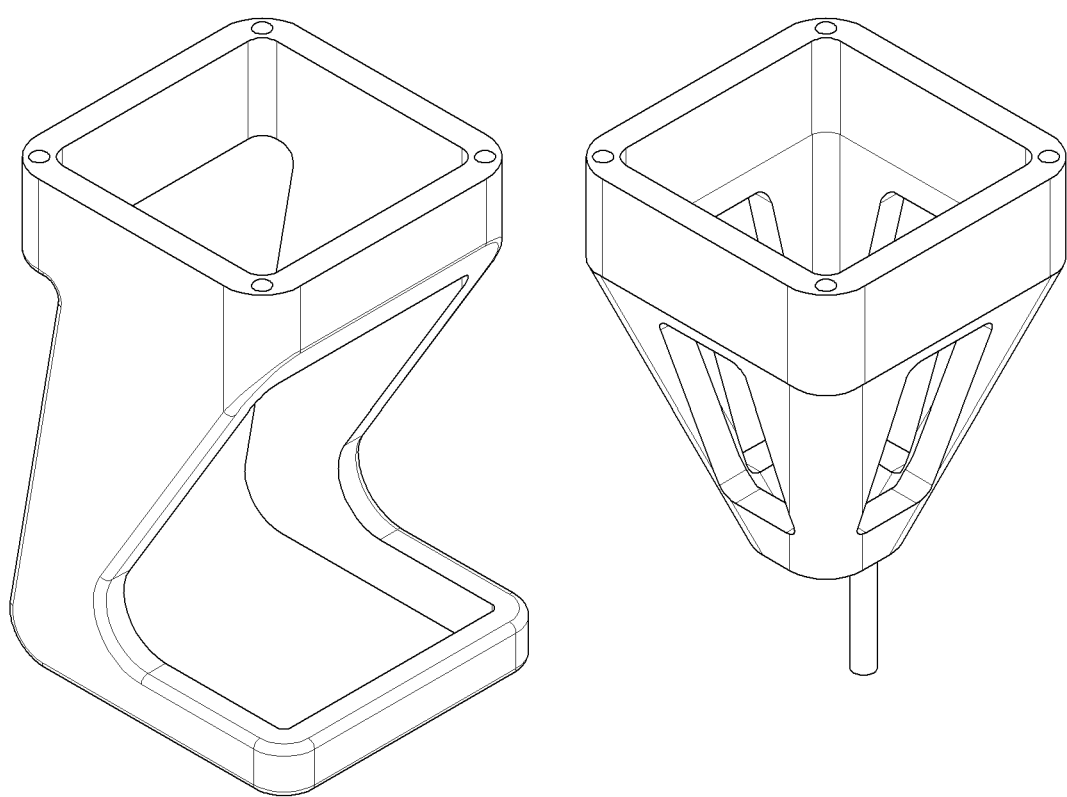
FIG. 17 illustrates photo images showing various structures of an end tool member applicable to a handpiece for skin laser treatment according to an example embodiment.

FIG. 17 illustrates photo images showing various structures of an end tool member applicable to a handpiece for skin laser treatment according to an example embodiment.

Referring to FIG. 17, the end tool member on the left corresponds to or is similar to the end tool member 120 of FIG. 4 and may be advantageously used when irradiating laser in a relatively wide area. The end tool member on the right is a type with a sharp end and may be advantageously used when irradiating laser to a single point. In addition, the structure of the end tool member may be variously modified.

According to the aforementioned example embodiments, it is possible to implement a handpiece for skin laser treatment that may improve a procedure characteristic and also improve a pain relief effect of a patient (i.e., minimize pain of the patient) by allowing a user (an operator) to easily control a spray range (area) of refrigerant according to the intention of the user (operator). Also, according to the example embodiments, it is possible to implement a handpiece for skin laser treatment that may accomplish an optimal procedure and a cooling effect in various laser treatment methods by easily controlling a spray direction, an angle, a spray amount, and a flowrate (i.e., spray intensity) of the refrigerant as well as a spray range of refrigerant. It is possible to implement a medical laser treatment apparatus having excellent performance and control functions by applying the handpiece according to the example embodiment.

In the case of using a handpiece and medical laser treatment apparatus according to an example embodiment, it is possible to reduce a procedure time and cost and to lower work intensity of an operator. Also, in the case of using a handpiece and a medical laser treatment apparatus according to an example embodiment, it is possible to reduce pain of a patient by easily and precisely adjusting an area of refrigerant spray. Also, in the case of using a handpiece and a medical laser treatment apparatus according to an example embodiment, it is possible to prevent refrigerant from being unnecessarily sprayed in an area outside a procedure and to reduce the occurrence of risk, such as frostbite, caused by direct contact between the refrigerant and the skin. Also, in the case of using a handpiece and a medical laser treatment apparatus according to an example embodiment, it is possible to improve the problem of reduced treatment effectiveness due to the water absorption of the laser and use laser energy more efficiently by implementing the maximum efficiency of refrigerant in an appropriate amount according to a procedure. Also, in the case of using a handpiece and a medical laser treatment apparatus according to an example embodiment, it is possible to save refrigerant being unnecessarily wasted, to improve economic feasibility, and to enhance environmental issues by accurately spraying the refrigerant only in a targeted spot area in which laser is irradiated through adjustment of a spray amount and spray range of the refrigerant.

In the present specification, example embodiments are disclosed and although specific terms are used, they are only used in general sense to easily describe technical details of the present invention and in general sense to easily describe the technical contents of the present invention and to help understanding of the present invention and do not limit the scope of the present invention. It is obvious to one of ordinary skill in the art that other modifications based on the technical spirit of the present invention may be made in addition to the example embodiments disclosed herein. For example, one of ordinary skill in the art may know that a handpiece for skin layer treatment according to the example embodiments described with reference to FIGS. 1 to 17 and a medical laser treatment device including the same may be variously modified. Therefore, the scope of the present invention may not be determined by the example embodiments and may need to be defined. by the technical spirit described in the claims.

What is claimed is:

1. A handpiece for skin laser treatment, the handpiece comprising:
   a handpiece body including a laser irradiation portion for irradiating a laser beam to a treatment target area of a skin of a person to be treated and a refrigerant spraying portion for spraying a refrigerant in the treatment target area; and
   an end tool member provided at an end of the handpiece body and configured to maintain a distance between the laser irradiation portion and a skin contact portion of the end tool member in contact with the skin of the person to be treated and to at least partially limit a target area corresponding to the treatment target area,
   wherein the refrigerant spraying portion includes a refrigerant spray nozzle having a refrigerant outlet for discharging the refrigerant toward the target area; and a nozzle positioning member configured to connect to the refrigerant spray nozzle and to adjust a distance between the refrigerant spray nozzle and the target area by changing a position of the refrigerant spray nozzle,
   a range of the refrigerant that is sprayed to the skin of the person to be treated is configured to be controllable by adjusting the distance between the refrigerant spray nozzle and the target area using the nozzle positioning member,
   the refrigerant spray nozzle has a first hollow hole through which the refrigerant passes and a first spiral portion is provided on an inner surface of the first hollow hole,
   the nozzle positioning member has a second hollow hole which the refrigerant passes through and communicates with the first hollow hole,
   the nozzle positioning member includes a threaded insertion portion configured to be inserted into the first hollow hole and to be coupled with the refrigerant spray nozzle and having a second spiral portion engaged with the first spiral portion on its outer circumferential surface and an adjustment head provided at an upper end of the threaded insertion portion, and
   the distance between the refrigerant spray nozzle and the target area is configured to be adjustable by rotating the adjustment head.

2. The handpiece of claim 1, further comprising:
   a fixing member configured to prevent rotation of the refrigerant spray nozzle on an outer surface of the refrigerant spray nozzle and to allow linear displacement in a longitudinal direction of the refrigerant spray nozzle.

3. The handpiece of claim 1, wherein the refrigerant spray nozzle further includes a spray amount adjustment unit for adjusting a spray amount of the refrigerant, and
   a size of the refrigerant outlet is controlled by the spray amount adjustment unit.

4. The handpiece of claim 3, wherein the spray amount adjustment unit comprises:

an opening limiting member configured to limit an opening area and having a plurality of guide grooves formed around the opening area;

a plurality of outlet adjustment plates configured to couple with the opening limiting member, and provided to be in contact with each other to define the refrigerant outlet with respect to the opening area and to connect to the plurality of guide grooves, respectively; and a rotatable control member configured to move the plurality of outlet adjustment plates along the plurality of guide grooves, and a size of the refrigerant outlet is configured to be controlled by moving the plurality of outlet adjustment plates along the plurality of guide grooves using the rotatable control member.

5. The handpiece of claim 4, wherein each of the plurality of outlet adjustment plates has a fan shape or a triangular shape, each of the plurality of guide grooves has an arc-shaped structure or a rectilinear structure, and each of the plurality of guide grooves has one end closer to the opening area than the other end and is formed to be farther from the opening area toward the other end.

6. The handpiece of claim 4, wherein the rotatable control member is controlled in a manual manner.

7. The handpiece of claim 4, wherein the rotatable control member is controlled in an electrical manner.

8. The handpiece of claim 1, wherein the refrigerant spraying portion is configured to spray the refrigerant in a direction that forms an angle of about 20° to 45° relative to an irradiation direction of the laser beam.

9. The handpiece of claim 1, further comprising:

a tilting device configured to tilt the refrigerant spraying portion, wherein a spray direction of the refrigerant is controlled by tilting the refrigerant spraying portion using the tilting device.

10. The handpiece of claim 1, wherein the laser irradiation portion is configured to irradiate a $CO_2$ laser beam.

11. A medical laser treatment apparatus comprising the handpiece of claim 1.

12. The medical laser treatment apparatus of claim 11, wherein the medical laser treatment apparatus comprises a device body configured to connect to the handpiece; and a connecting arm configured to connect between the device body and the handpiece, and the device body comprises a laser generator configured to generate the laser beam and a refrigerant supply configured to supply the refrigerant.

* * * * *